(12) United States Patent
Ito

(10) Patent No.: US 10,413,484 B2
(45) Date of Patent: Sep. 17, 2019

(54) PRINTING DEVICE, METHOD FOR PRINTING, AND NON-TRANSITORY COMPUTER READABLE MEDIUM STORING PROGRAM CAUSING COMPUTER TO EXECUTE PROCESS FOR PRINTING

(71) Applicant: FUJI XEROX CO., LTD., Tokyo (JP)

(72) Inventor: Kensuke Ito, Yokohama (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 15/767,973

(22) PCT Filed: Apr. 15, 2016

(86) PCT No.: PCT/JP2016/062175
§ 371 (c)(1),
(2) Date: Apr. 12, 2018

(87) PCT Pub. No.: WO2017/085950
PCT Pub. Date: May 26, 2017

(65) Prior Publication Data
US 2018/0303715 A1 Oct. 25, 2018

(30) Foreign Application Priority Data
Nov. 18, 2015 (JP) ................................. 2015-225263

(51) Int. Cl.
*A61J 3/00* (2006.01)
*A61J 3/06* (2006.01)
(Continued)

(52) U.S. Cl.
CPC ................. *A61J 3/007* (2013.01); *A61J 3/06* (2013.01); *B41J 2/01* (2013.01); *B41J 3/407* (2013.01); *G06T 7/00* (2013.01); *G06T 7/0002* (2013.01)

(58) Field of Classification Search
CPC .......... A61J 3/007; A61J 3/06; G06T 7/0002; G06T 7/00; B41J 3/407; B41J 2/01
See application file for complete search history.

(56) References Cited

U.S. PATENT DOCUMENTS

2013/0088555 A1 4/2013 Hanina et al.
2014/0168309 A1 6/2014 Morita et al.
(Continued)

FOREIGN PATENT DOCUMENTS

EP 2829260 A1 1/2015
EP 2875802 A1 5/2015
(Continued)

OTHER PUBLICATIONS

IP.com search (Year: 2019).*
(Continued)

*Primary Examiner* — Lisa Solomon
(74) *Attorney, Agent, or Firm* — Oliff PLC

(57) ABSTRACT

A first image pickup unit picks up a first image including a conveyed object. A printing unit performs printing on the object based on the first image. A second image pickup unit picks up a second image including the object on which printing has been performed. A check unit checks a print state of the object in the second image. A first acquisition unit acquires feature data from one of the first image and the second image, as registration data. A second acquisition unit acquires feature data from the other image of the first image and the second image, as collation data. A verification unit compares the registration data and the collation data and verifies that reliability of the registration data is equal to or greater than a predetermined criterion value. A storage stores the registration data as data for determining an identity of the object.

20 Claims, 35 Drawing Sheets

(51) Int. Cl.
*G06T 7/00* (2017.01)
*B41J 2/01* (2006.01)
*B41J 3/407* (2006.01)

(56) References Cited

U.S. PATENT DOCUMENTS

| | | | |
|---|---|---|---|
| 2014/0260104 A1 | 9/2014 | Ackley et al. | |
| 2015/0140289 A1* | 5/2015 | Ferro | G03F 7/0046 428/195.1 |
| 2016/0004934 A1 | 1/2016 | Ebata et al. | |
| 2016/0229198 A1* | 8/2016 | Izume | B41F 33/0045 |

FOREIGN PATENT DOCUMENTS

| | | |
|---|---|---|
| JP | 4103826 B2 | 6/2008 |
| JP | 2013-013711 A | 1/2013 |
| JP | 2013-121432 A | 6/2013 |
| JP | 2014-191361 A | 10/2014 |
| WO | 2010/072745 A1 | 7/2010 |

OTHER PUBLICATIONS

Jul. 5, 2016 International Search Report issued in International Patent Application No. PCT/JP2016/062175.

Jul. 5, 2016 Written Opinion of the International Searching Authority issued in International Patent Application No. PCT/JP2016/062175.

Jun. 6, 2019 extended European Search Report issued in Application No. 16865953.0.

* cited by examiner

81
REGISTRATION DATA ACQUISITION REGION

REGISTRATION DATA

32X32 DOTS

82
COLLATION DATA ACQUISITION REGION

COLLATION DATA

64X64 DOTS

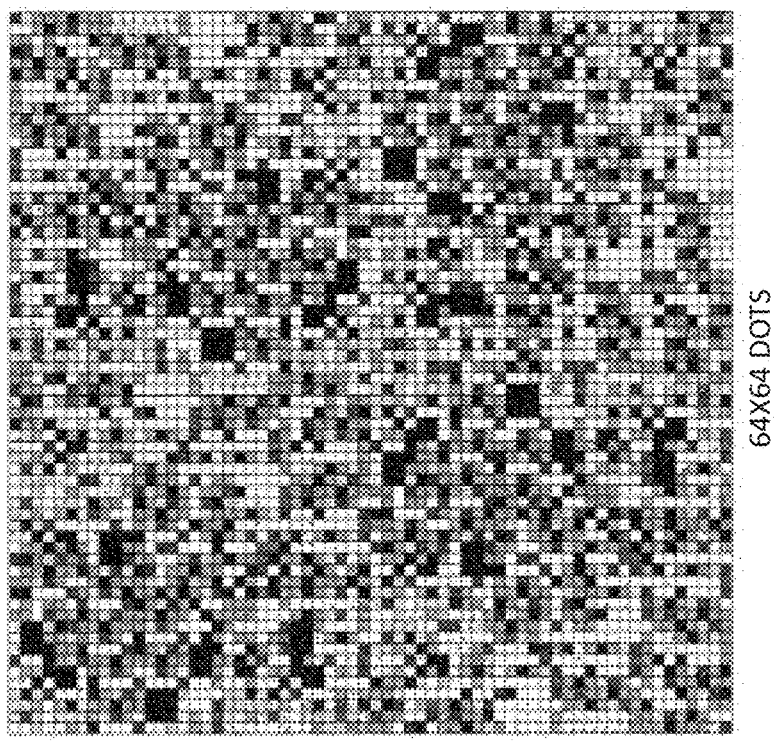
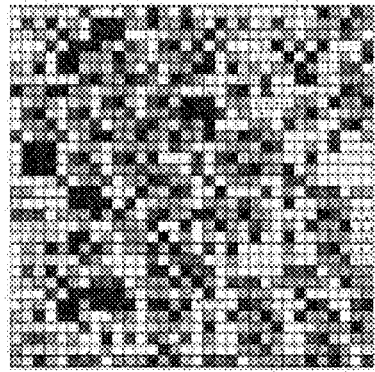
FIG. 14

FIG. 15
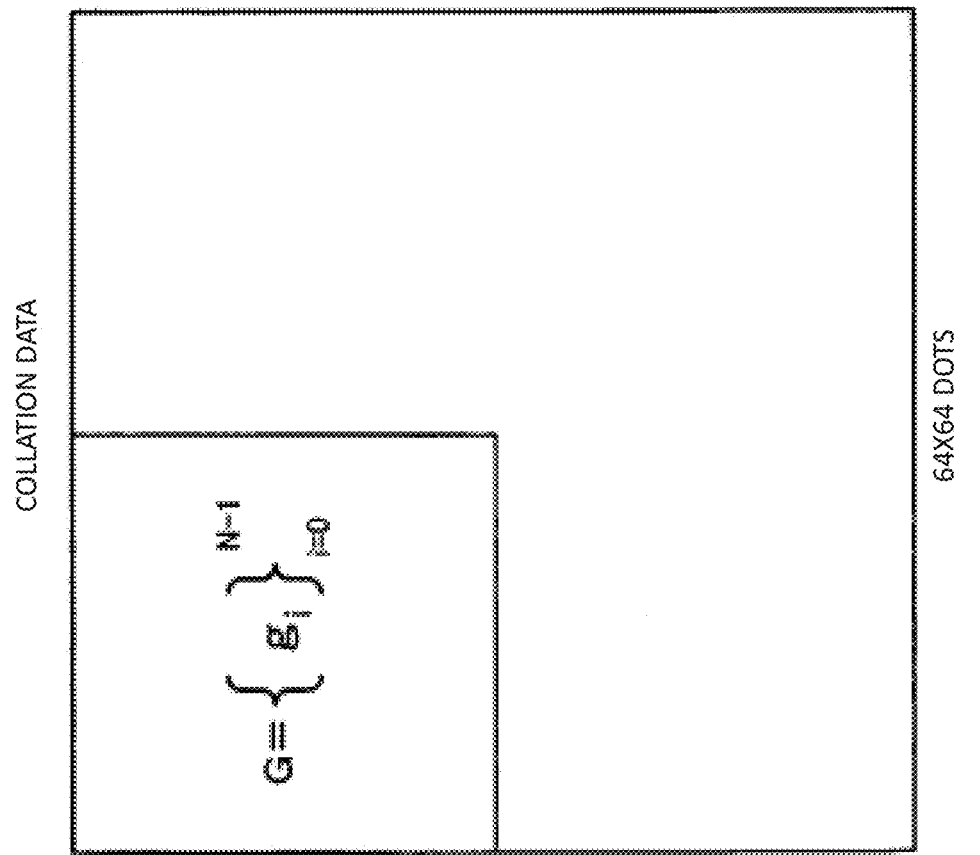
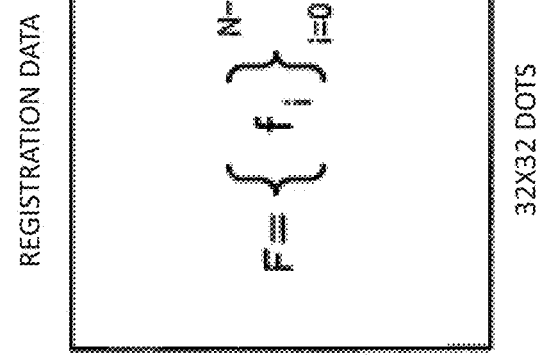

③＞②＞①

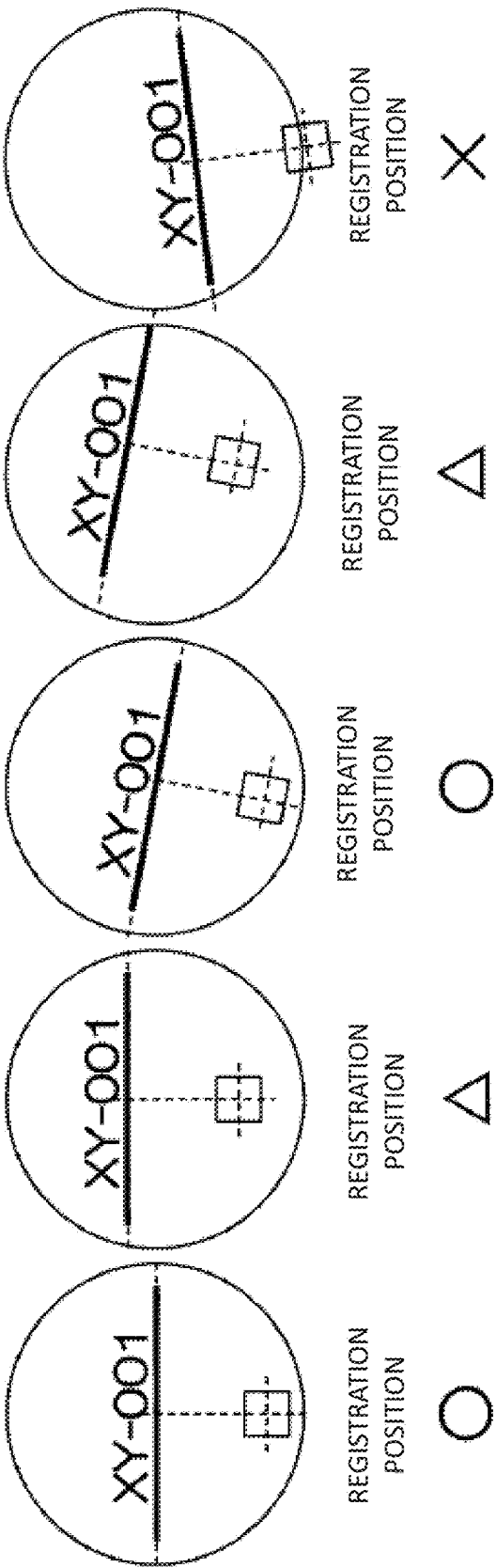

CASE WHERE ACQUISITON REGION OF REGISTRATION DATA IS DEFINED BASED ON PRINTING ATTERN AND OUTER SHAPE

PRINTING DEVICE, METHOD FOR PRINTING, AND NON-TRANSITORY COMPUTER READABLE MEDIUM STORING PROGRAM CAUSING COMPUTER TO EXECUTE PROCESS FOR PRINTING

CROSS-REFERENCE TO RELATED APPLICATIONS

This application is based on and claims priority under 35 USC 119 from Japanese Patent Application No. 2015-225263 filed on Nov. 18, 2015.

BACKGROUND

Technical Field

The present invention relates to a printing device, a method, and a program.

Related Art

There are unique random patterns like the fingerprint of a human, a vein pattern, an iris pattern on surfaces of various objects such as paper, tablets, metal, and resin. Therefore, a technology in which an image of a portion of a random pattern distributed on the surface of an object is acquired and the acquired image is registered as registration data, and then image data of a random pattern, which is acquired from an object again is compared to the registration data so as to determine whether or not the objects are the same as each other has been proposed.

In the technology, authenticity is determined by determining whether or not the registered registration data coincides with collation data acquired from an object as a determination target.

SUMMARY

According to an aspect of the present invention, there is provided a printing device which includes: a first image pickup unit that picks up a first image including a conveyed object; a printing unit that performs printing on the object based on the first image; a second image pickup unit that picks up a second image including the object on which printing has been performed by the printing unit, a check unit that checks a print state of the object in the second image; a first acquisition unit that acquires feature data indicating a feature distributed in a first region of a predetermined size on the object, from one of the first image and the second image, as registration data; a second acquisition unit that acquires feature data indicating a feature distributed in a second region of a predetermined size on the object, from the other image of the first image and the second image, as collation data; a verification unit that compares the registration data and the collation data and that verifies that reliability of the registration data is equal to or greater than a predetermined criterion value; and a storage that stores the registration data as data for determining an identity of the object.

BRIEF DESCRIPTION OF DRAWINGS

Exemplary embodiment(s) of the present invention will be described in detail based on the following figures, wherein:

FIG. 14 is a diagram illustrating an example of the registration data and the collation data as a target of a collation operation;

FIG. 15 is a diagram illustrating a form in which data having the same size as the registration data is sequentially cut out from the collation data;

FIGS. 32A to 32E are diagrams illustrating examples of cases where an acquisition region of the registration data is determined based on only a printing pattern;

DETAILED DESCRIPTION

Hereinafter, embodiments of the present invention will be described in detail with reference to the drawings.

First Embodiment

Figure 1:
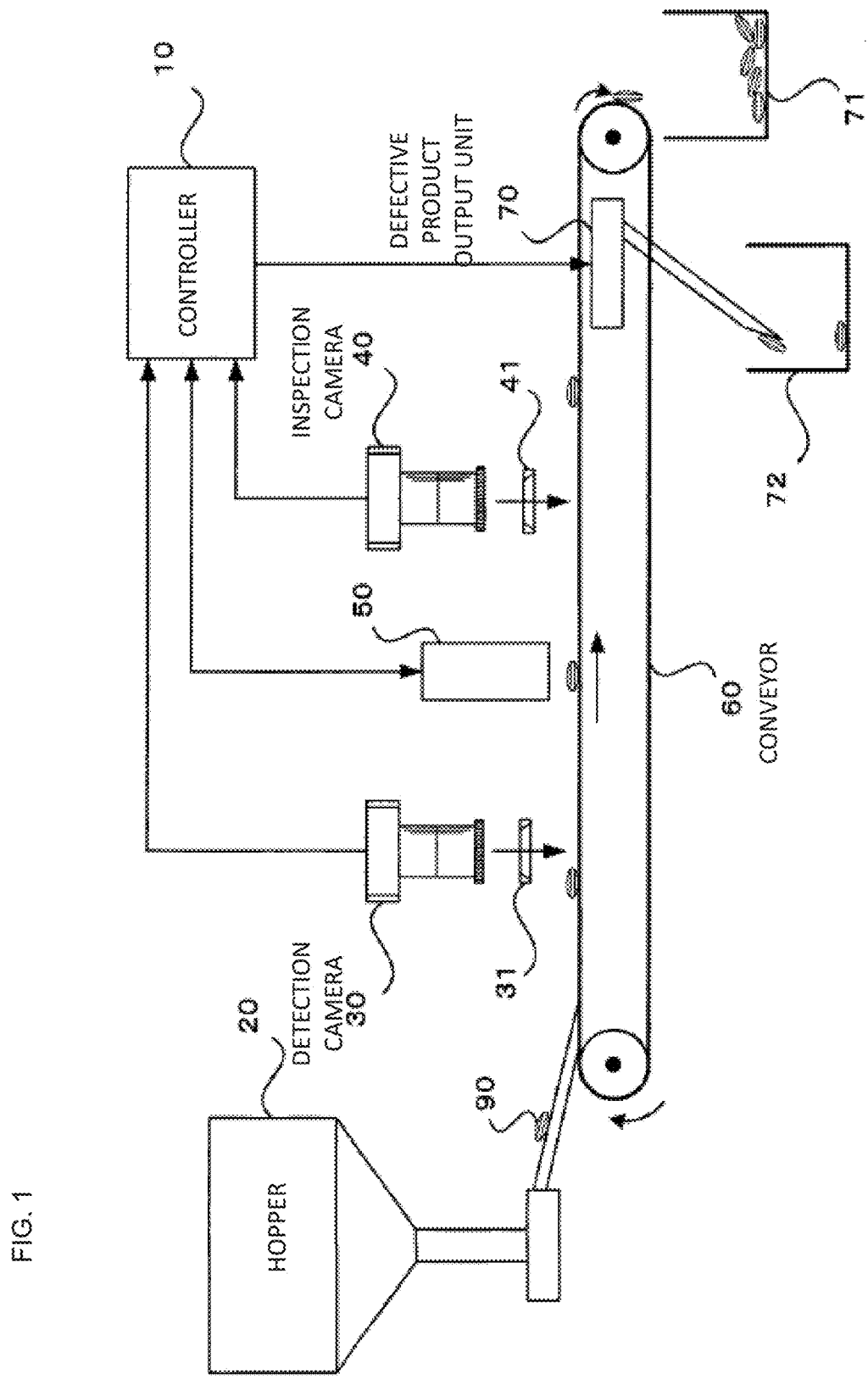
FIG. 1 is a diagram illustrating a configuration of a printing device according to a first embodiment of the present invention.

Firstly, a printing device according to a first embodiment of the present invention will be described. FIG. 1 is a diagram illustrating a configuration of the printing device in the first embodiment of the present invention.

In the exemplary embodiment, in the printing device that prints print information such as characters, on a circular tablet, feature data which allows the tablet to be uniquely specified when printing is performed on the tablet is acquired and stored as registration data (registration image data).

In this manner, pieces of registration data of all tablets on which printing has been performed are acquired and stored. Thus, for example, in a case where a tablet suspected to be counterfeit is found in the market, feature data of the tablet which has been suspected to be counterfeit and collected is acquired and is compared to all pieces of stored registration data, and thus it can be determined whether the tablet is a tablet which has been regularly manufactured and shipped or a counterfeit tablet.

In the exemplary embodiment, a case where printing is performed on a circular tablet will be described. However, the present invention can be similarly applied to a tablet having a shape other than a circular shape. Also regarding the type of tablets, the present invention can be applied to any of FC (film coat) tablets, coating tablets of, for example, sugar coating, plain tablets (core tablets).

In the present invention, a circular tablet is used as an example of an object. However, the present invention can be also applied to cases using various objects, for example, chip components such as a chip capacitor, components such as gears and washers, IC chips, semiconductor components, credit cards, tickets, securities, and documents, so long as a random readable unique feature such as fine unevenness on a surface of the object is distributed on the surface.

As illustrated in FIG. 1, the printing device in the exemplary embodiment includes a controller 10, a hopper 20 configured to supply a tablet 90, a detection camera 30, a ring lighting unit 31, an inspection camera 40, a ring lighting unit 41, a print head section 50, a conveyor (conveying path) 60 configured to convey the tablet 90 supplied by the hopper 20, a defective product output unit 70, a non-defective product storing box 71, and a defective product storing box 72.

The ring lighting units 31 and 41 are lighting devices that irradiate the tablet 90 conveyed on the conveyor 60, with light.

The detection camera 30 is an image pickup unit that picks up an image (first image) including a tablet conveyed on the conveyor 60. The detection camera 30 is provided right over the ring lighting unit 31, and thus can pick up an image of the tablet 90 irradiated with light by the ring lighting unit 31. Thus, it is possible to detect the position, the orientation, and the like of the tablet by the detection camera 30 picking up an image of the tablet 90.

The print head section 50 is a printing unit that performs printing on the tablet 90 based on the image picked up by the detection camera 30. Here, the print head section 50 prints, for example, characters, numbers, and symbols such as a manufacturer serial number, a lot number, and a product name, on the tablet 90 conveyed on the conveyor 60 in an ink jet method.

Specifically, the controller 10 controls a printing operation of the print head section 50. The controller 10 detects information of, for example, the position or the orientation of the tablet 90, and the front or back surface thereof, based on the image picked up by the detection camera 30. The controller 10 controls the print head section 50 at a timing, based on the detected information, when characters and the like are printed at the designated position on the tablet 90 on the conveyor 60.

In the exemplary embodiment, the tablet 90 is a circular tablet having no secant line. Thus, it is not necessary to detect information of the orientation or the front or back surface. However, in a case where printing is performed on a circular tablet having a secant line, it is determined whether the surface is the front surface or the back surface, based on the orientation of the tablet on the conveyor 60 or determination of whether or not a secant line is provided on the tablet. A printing controller 21 controls the orientation and the like of characters to be printed, based on the determination result.

The inspection camera 40 is an image pickup unit that picks up an image (second image) including the tablet 90 after printing is performed by the print head section 50. The inspection camera 40 is provided right over the ring lighting unit 41 and can pick up an image of the tablet 90 irradiated with light by the ring lighting unit 41. The inspection camera 40 is provided to detect and eliminating a tablet 90 having print defects such as printing deviation and printing blur.

The defective product storing box 72 is an output place for storing a tablet of a defective product which has been output by the defective product output unit 70. The non-defective product storing box 71 is a storing place for storing a tablet of a non-defective product which has not been output by the defective product output unit 70.

The defective product output unit 70 performs an operation of outputting a tablet 90 conveyed on the conveyor 60 to the defective product storing box 72, based on the control of the controller 10.

The controller 10 checks a print state of a tablet 90 in an image, based on the image picked up by the inspection camera 40. In a case when the controller 10 determines that the print state has a print defect, the controller 10 controls the defective product output unit 70 to output the tablet 90 as the defective product, to the defective product storing box 72.

Figure 2:
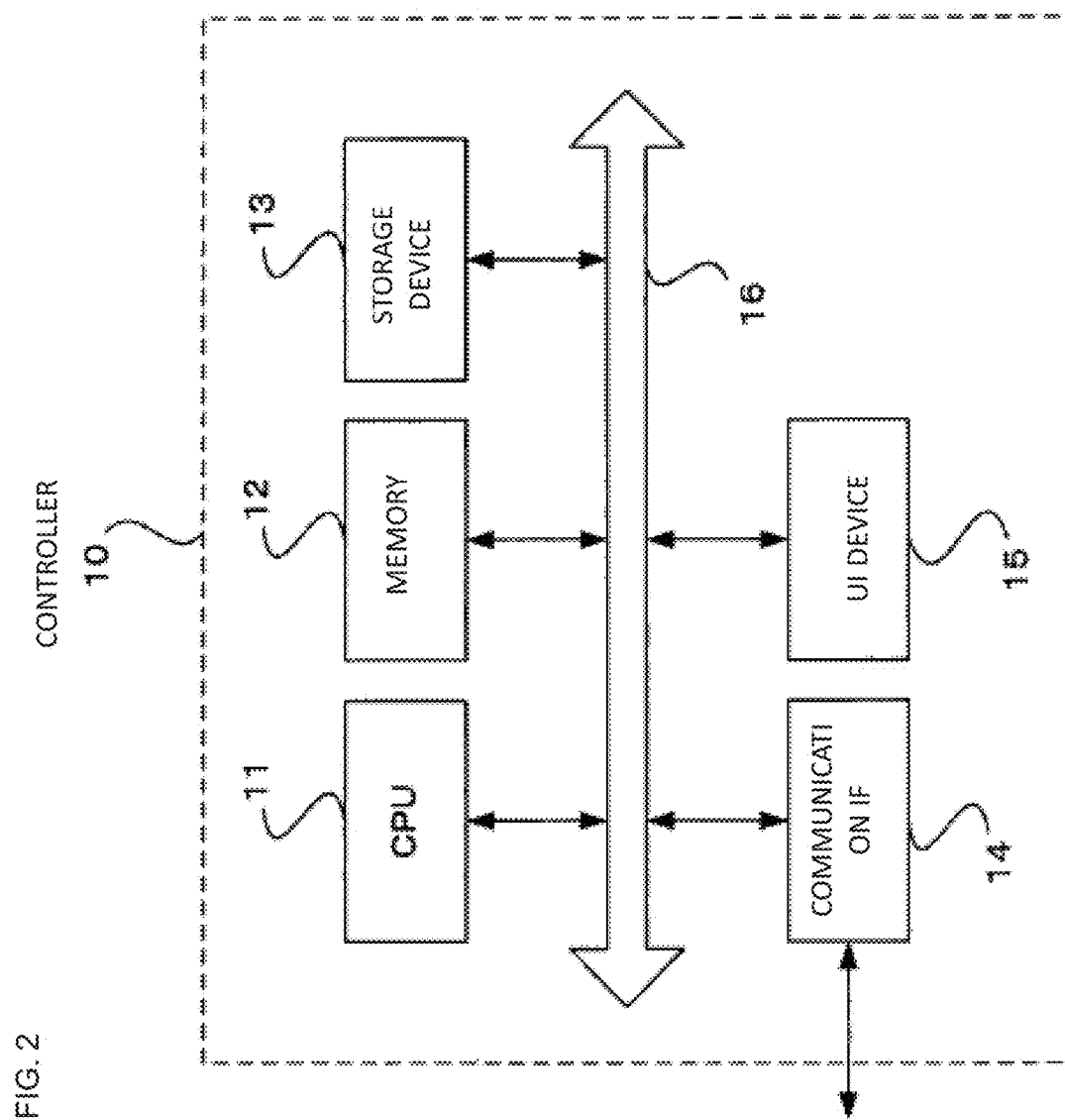
FIG. 2 is a block diagram illustrating a hardware configuration of a controller 10 in the first embodiment of the present invention.

Next, FIG. 2 illustrates the hardware configuration of the controller 10 in the printing device in the exemplary embodiment.

As illustrated in FIG. 2, the controller 10 includes a CPU 11, a memory 12, a storage device 13 such as a hard disk drive (HDD), a communication interface (IF) 14, and a user interface (UI) device 15. The IF 14 transmits and receives data to and from an external device such as the detection camera 30, the print head section 50, the inspection camera 40, and the defective product output unit 70. The UI device 15 includes a touch panel or a liquid crystal display with a keyboard. These components are connected to each other through a control bus 16.

The CPU 11 performs predetermined processing based on a control program stored in the memory 12 or the storage device 13, so as to control an operation of the controller 10. In the exemplary embodiment, descriptions will be made on the assumption that an example in which the CPU 11 reads and executes the control program stored in the memory 12 or the storage device 13. However, the program may be stored in a storage medium such as a CD-ROM and may be provided to the CPU 11.

Figure 3:
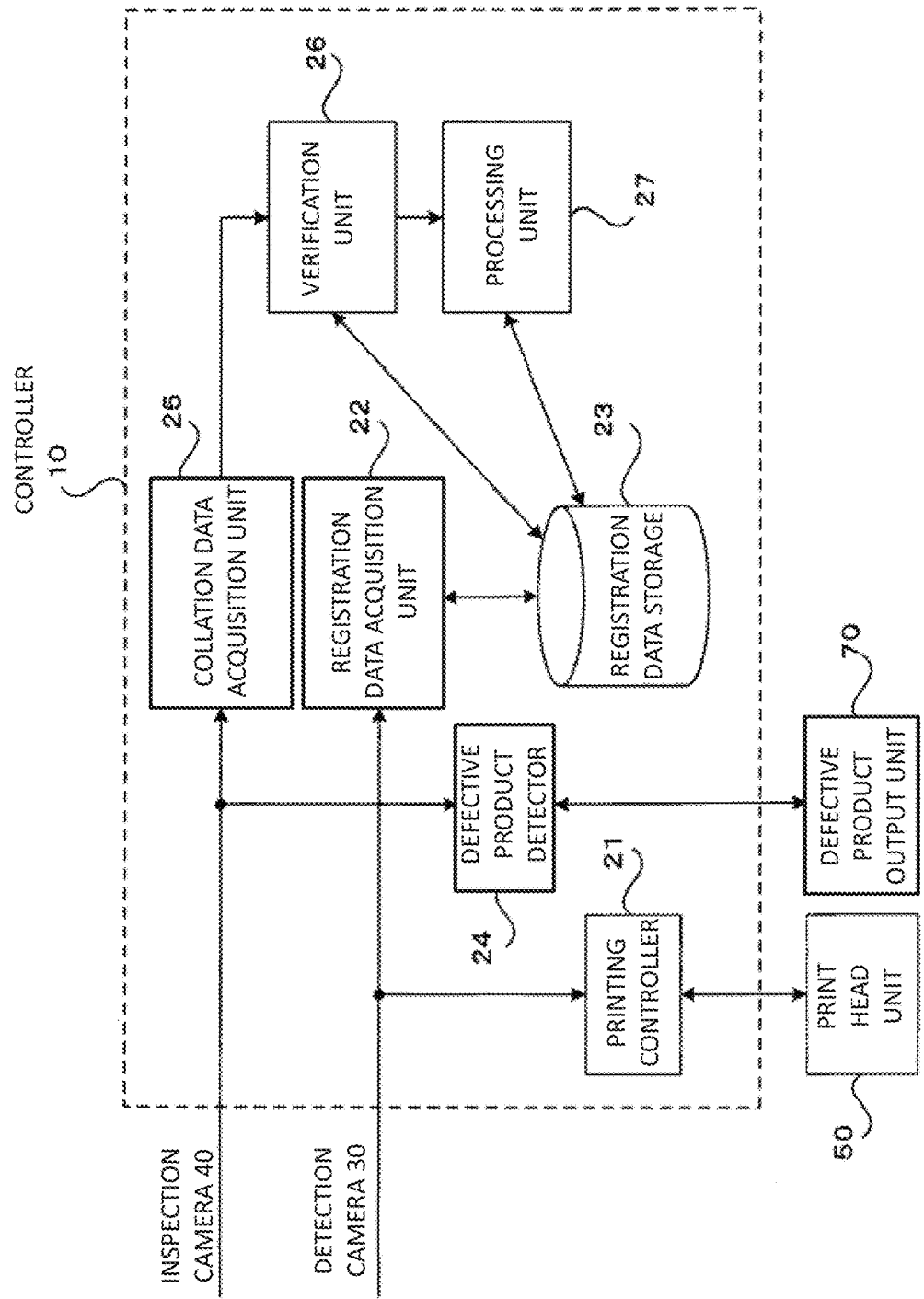
FIG. 3 is a block diagram illustrating a functional configuration of the controller 10 in the first embodiment of the present invention.

FIG. 3 is a block diagram illustrating a functional configuration of the controller 10, which is realized by executing the control program.

As illustrated in FIG. 3, the controller 10 in the exemplary embodiment includes the printing controller 21, a registration data acquisition unit 22, a registration data storage 23, a defective product detector 24, a collation data acquisition unit 25, a verification unit 26, and a processing section 27.

The printing controller 21 detects the position of a tablet 90 as a printing target, from an image picked up by the detection camera 30. The printing controller 21 controls a printing timing of the print head section 50 based on the detected position. That is, the printing controller 21 calculates a timing for outputting a print instruction to the print head section 50, based on information of the conveying speed of the conveyor 60, the position of the tablet 90 in the picked image, the printing speed of the print head section 50, and the like. The printing controller transmits the print instruction to the print head section 50 at the calculated timing.

The defective product detector 24 determines whether or not print information of characters and the like printed on a tablet 90 has a problem such as printing blur or printing deviation, from the image which has been picked up by the inspection camera 40 and includes the tablet 90 on which printing has been performed. In a case where it is determined that printing has a print defect, the defective product detector 24 controls the defective product output unit 70 to output the tablet 90 from the conveyor 60. The defective product detector 24 detects a problem such as a defect of a tablet 90 in addition to poor printing.

The registration data acquisition unit 22 acquires feature data indicating a feature distributed in a first region having a predetermined size on the surface of a tablet 90, as registration data, from an image picked up by the detection camera 30. Specifically, the registration data acquisition unit 22 acquires an image of 32 dots×32 dots in a registration data acquisition region which has been set on the tablet 90 in advance, as registration data.

Figure 4:
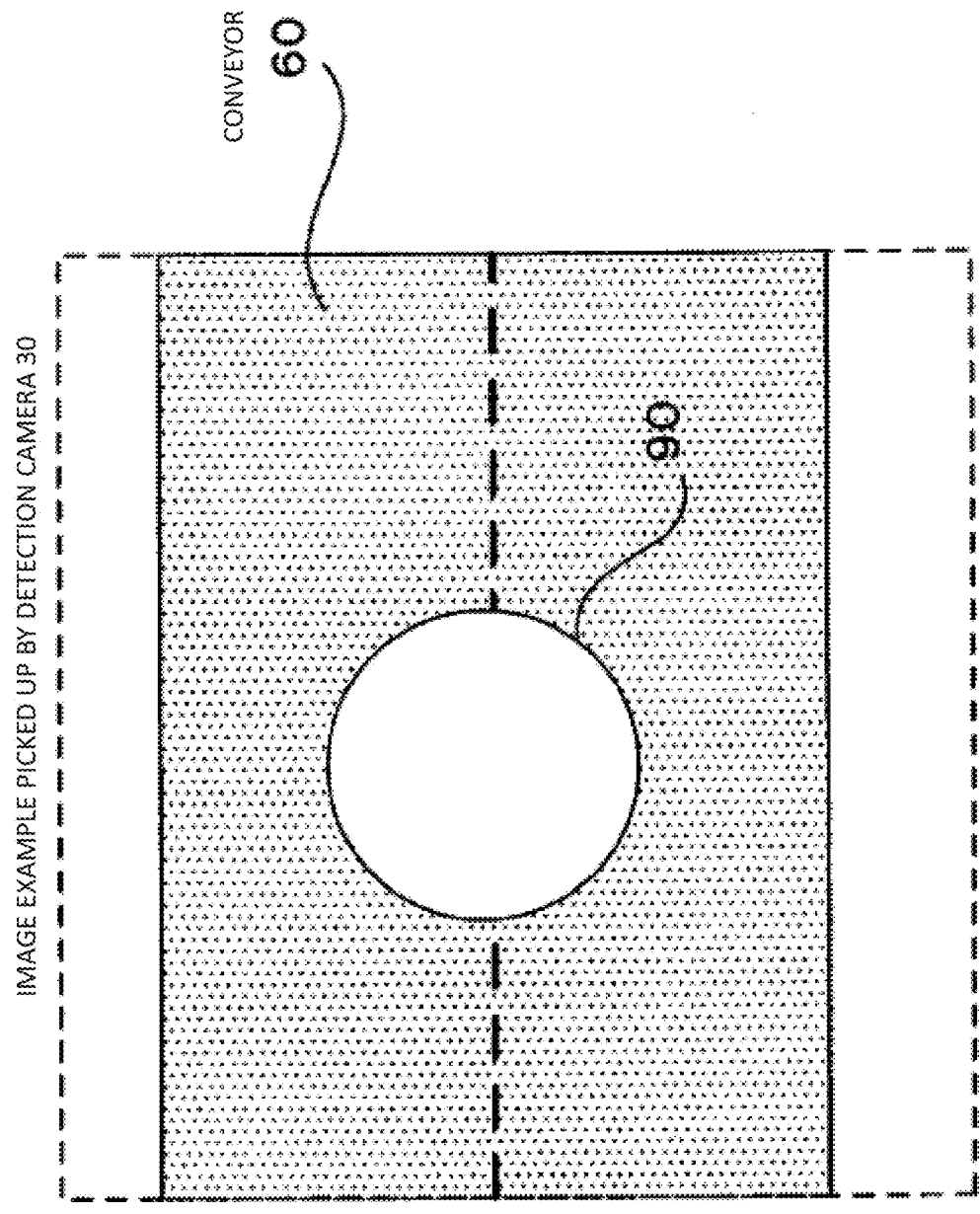
FIG. 4 is a schematic diagram illustrating an image picked up by a detection camera 30.
Figure 5:
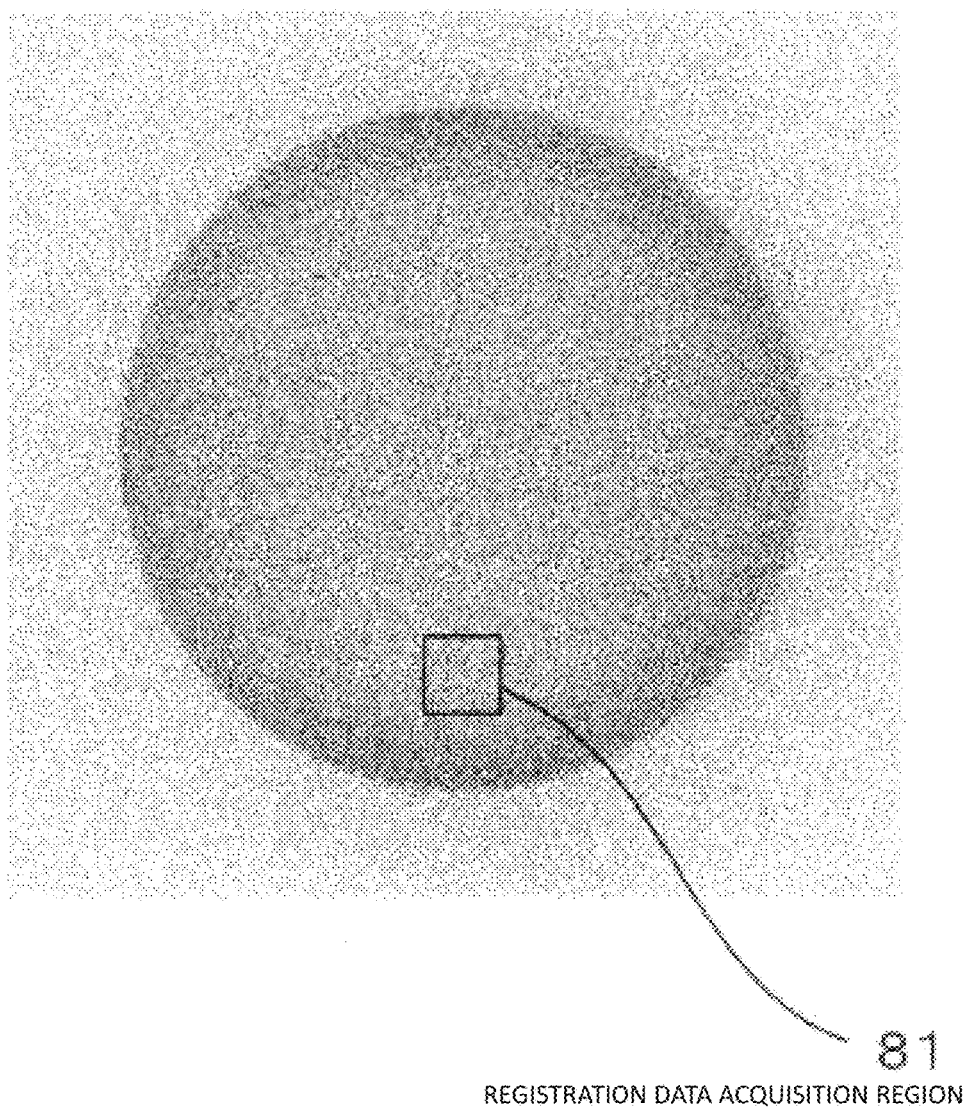
FIG. 5 is a diagram illustrating an example of an image of a tablet and an example of a position of a registration data acquisition region 81, which have been acquired in practice.

For example, FIG. 4 illustrates a schematic diagram of an image picked up by the detection camera 30. FIG. 5 illustrates an example of an image of a tablet, which has been acquired in practice, and an example of the position of a registration data acquisition region 81.

FIG. 4 illustrates a form in which an image including a tablet 90 on the conveyor 60 is picked up.

In FIG. 5, it is understood that the registration data acquisition region 81 is set at a predetermined position on the image of the tablet, which has been acquired in practice. Various methods for determining a position of the registration data acquisition region 81 to be a reference are provided. Here, a method of defining the position of predetermined characters to be printed on a tablet as the reference will be described.

Figure 6:
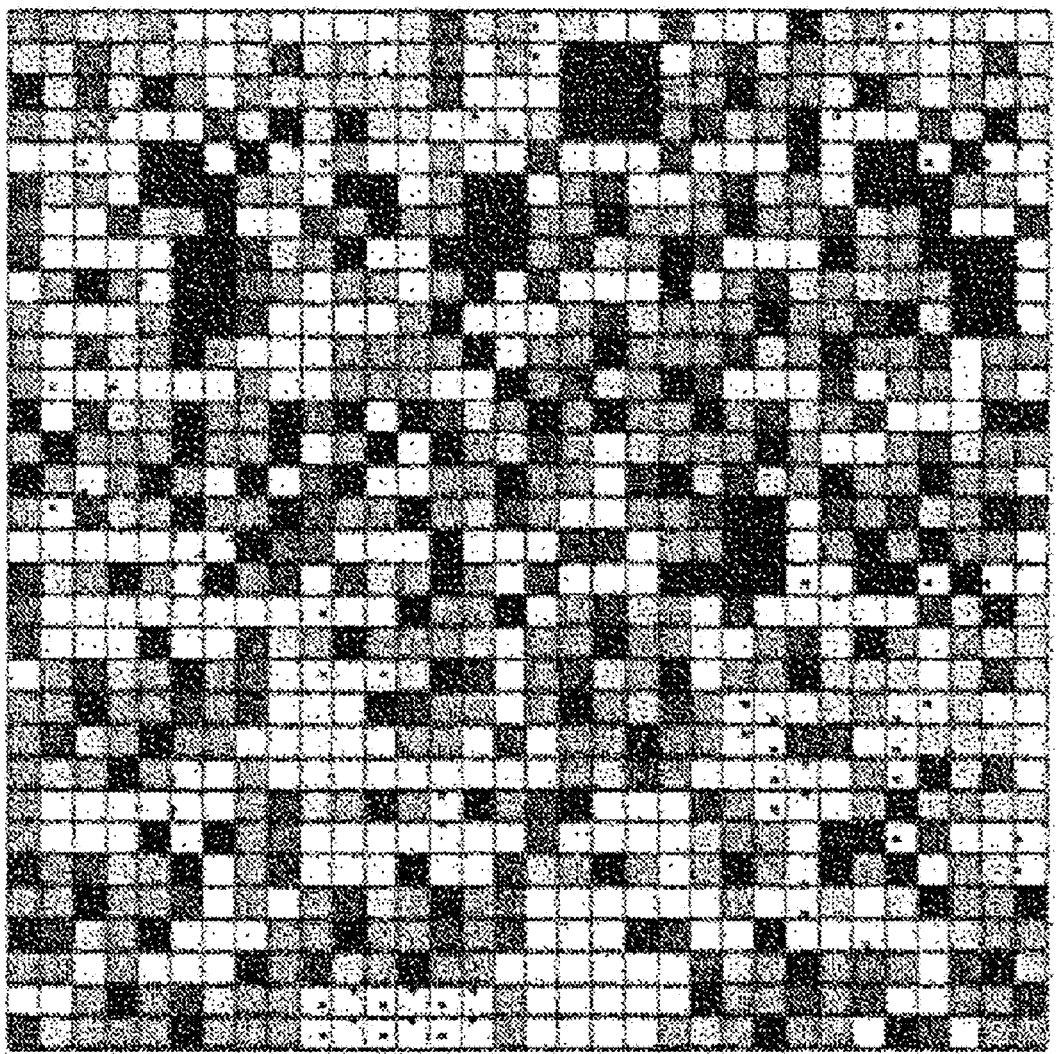
FIG. 6 is a diagram illustrating an example of the registration data.

FIG. 6 illustrates an example of registration data obtained by cutting out data of a region having a size of 32 dots×32 dots in the registration data acquisition region 81.

In the example of the registration data illustrated in FIG. 6, it is understood that a density value of each pixel of 1024 (32×32) dots is acquired as data.

The printing controller 21 controls the print head section 50 to perform processing of printing designated characters and the like on the tablet 90, based on the position of the tablet 90 in the image picked up by the detection camera 30.

Figure 7:
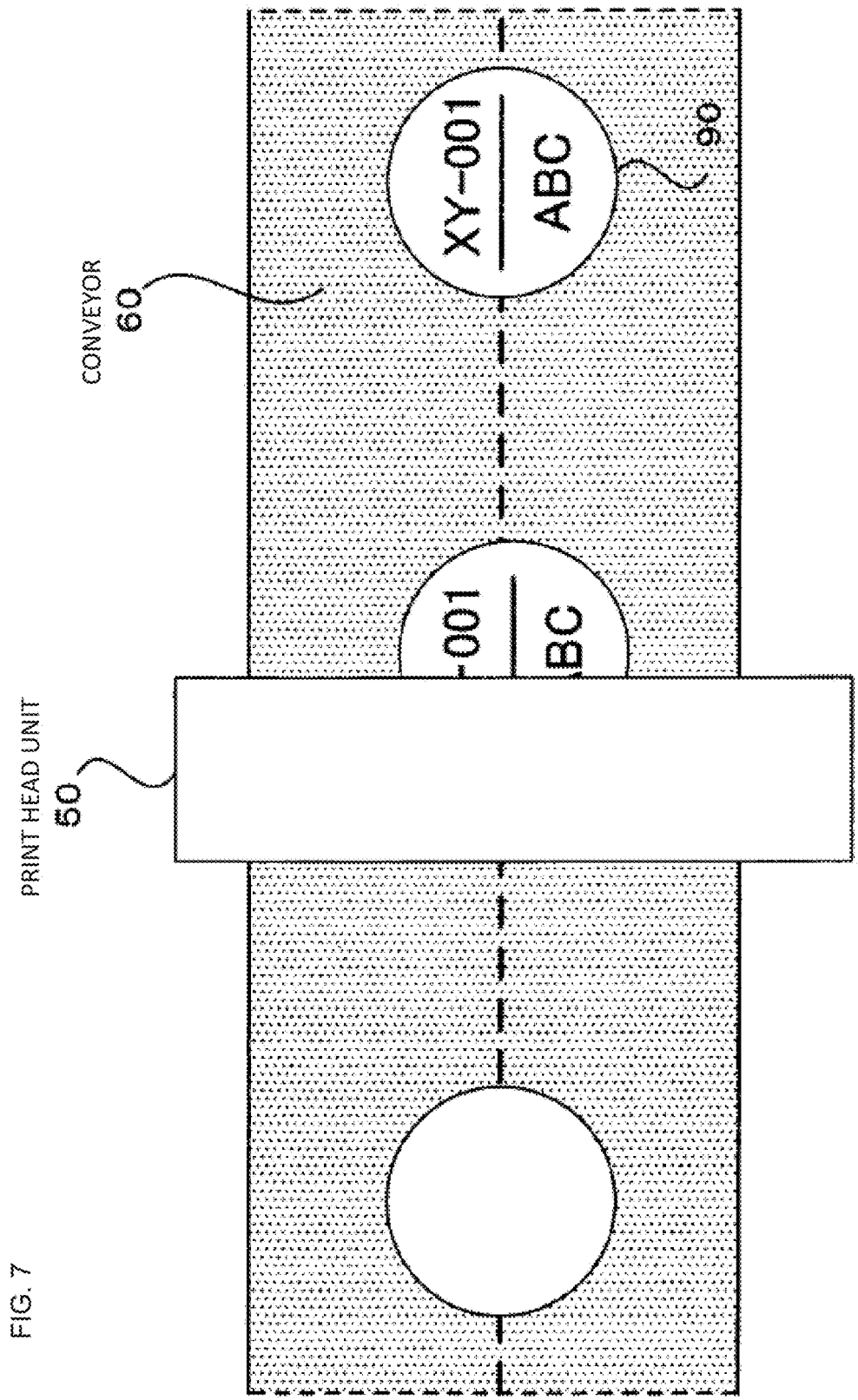
FIG. 7 is a diagram illustrating a form in which printing is performed by a print head section 50.

FIG. 7 illustrates a form in which printing is performed by the print head section 50 in this manner. With reference to FIG. 7, it is understood that characters of "XY-001" and "ABC" and a horizontal line are printed on the tablet 90 when the tablet 90 passes under the print head section 50 by the conveyor 60.

The collation data acquisition unit 25 acquires feature data indicating a feature distributed in a second region having a predetermined size on the tablet 90, as collation data (collation image data), from an image picked up by the inspection camera 40. The collation data acquisition unit 25 acquires feature data indicating a feature distributed in a collation data acquisition region (second region) which includes the registration data acquisition region (first region) 81 on the tablet and has a size larger than that of the registration data acquisition region 81, as collation data.

Specifically, the collation data acquisition unit 25 acquires an image of 64 dots×64 dots in the collation data acquisition region which has been set on the tablet 90 in advance, as the collation data.

Figure 8:
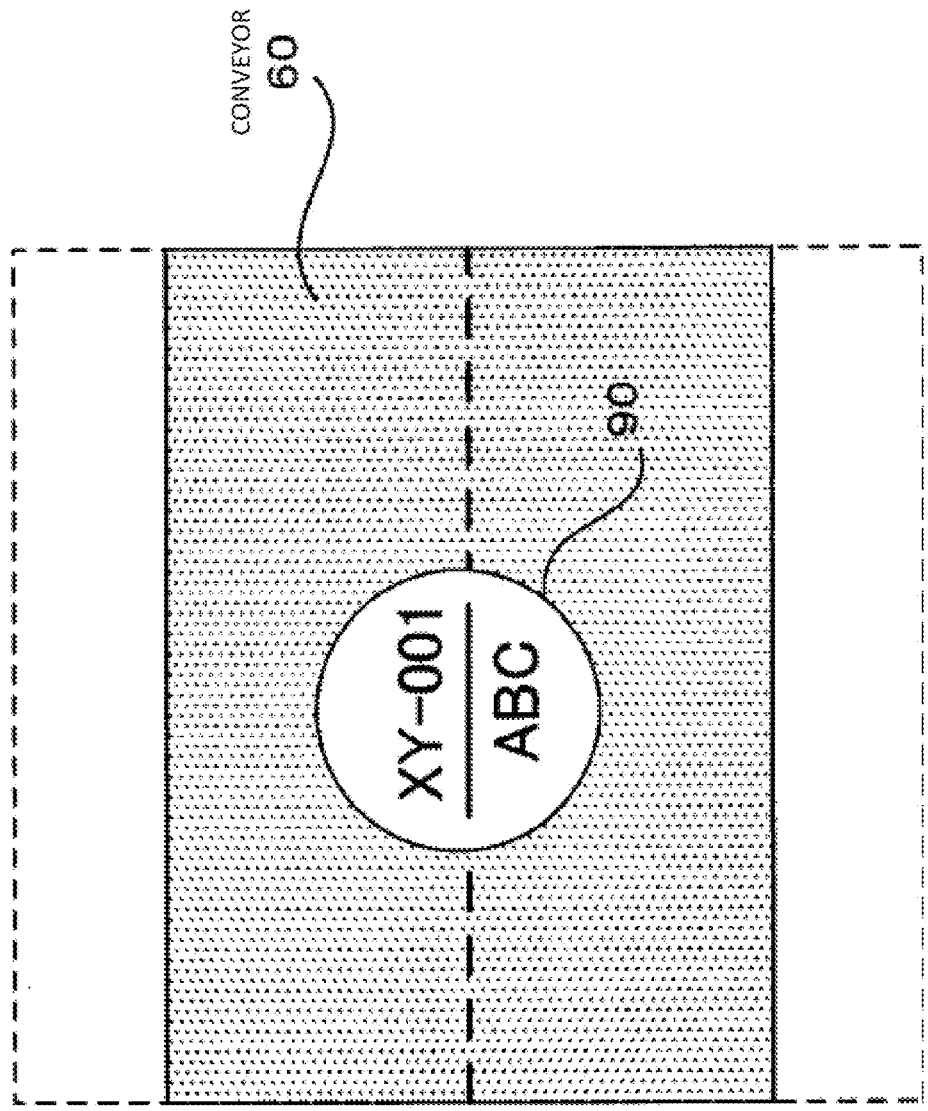
FIG. 8 is a schematic diagram illustrating an image picked up by an inspection camera 40.
Figure 9:
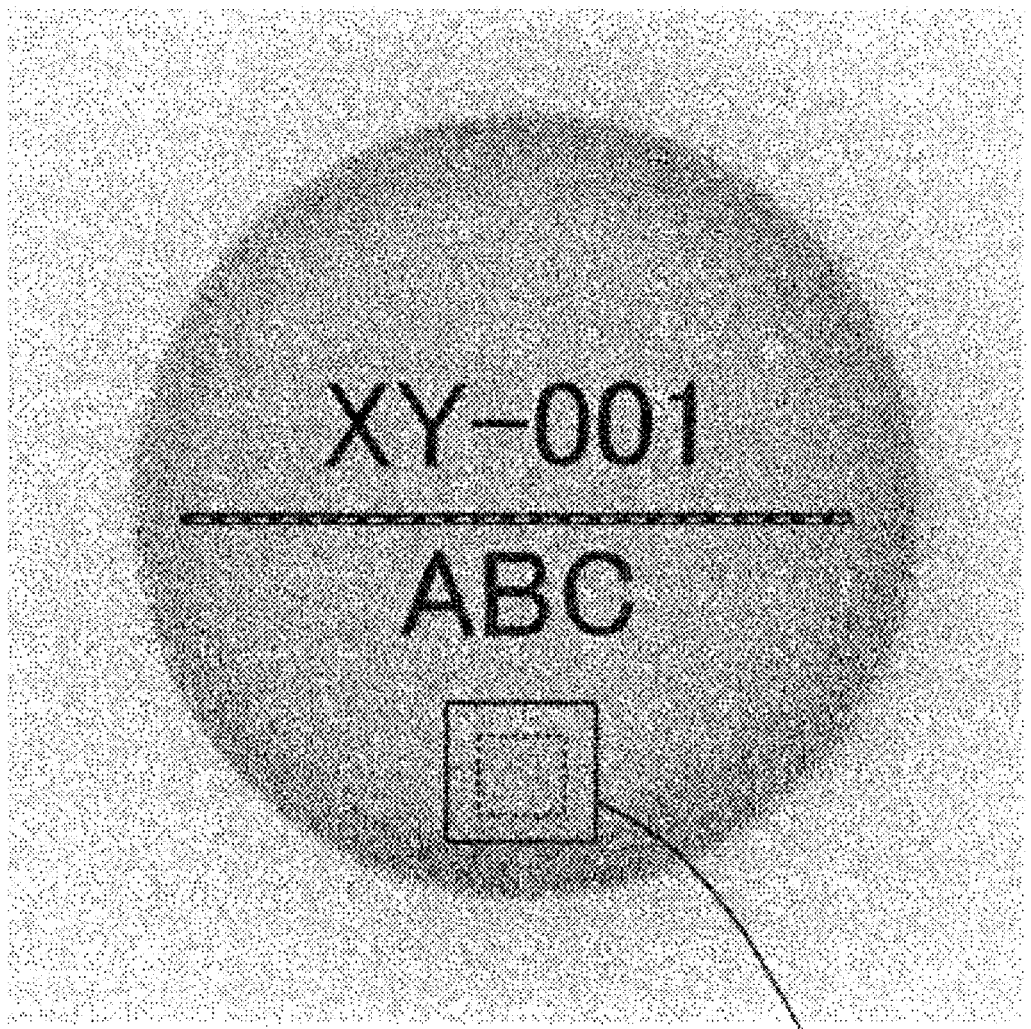
FIG. 9 is a diagram illustrating an example of an image of a tablet and an example of a position of a collation data acquisition region 82, which have been acquired in practice.

For example, FIG. 8 illustrates a schematic diagram of an image picked up by the inspection camera 40. FIG. 9 illustrates an example of an image of a tablet, which has been acquired in practice, and an example of the position of the collation data acquisition region 82.

FIG. 8 illustrates a form in which an image including a tablet 90 which is conveyed on the conveyor 60 and is subjected to printing is picked up.

In FIG. 9, it is understood that the collation data acquisition region 82 is set at a predetermined position on the image of the tablet, which has been acquired in practice. The collation data acquisition region 82 is set to be a wider region which includes the registration data acquisition region 81.

In the exemplary embodiment, the position of the registration data acquisition region 81 or the collation data acquisition region 82 is defined based on the position of print information such as characters, which has been printed. Therefore, here, the registration data acquisition region 81 and the collation data acquisition region 82 is defined based on the relative position from the horizontal line printed on the tablet.

Figure 10:
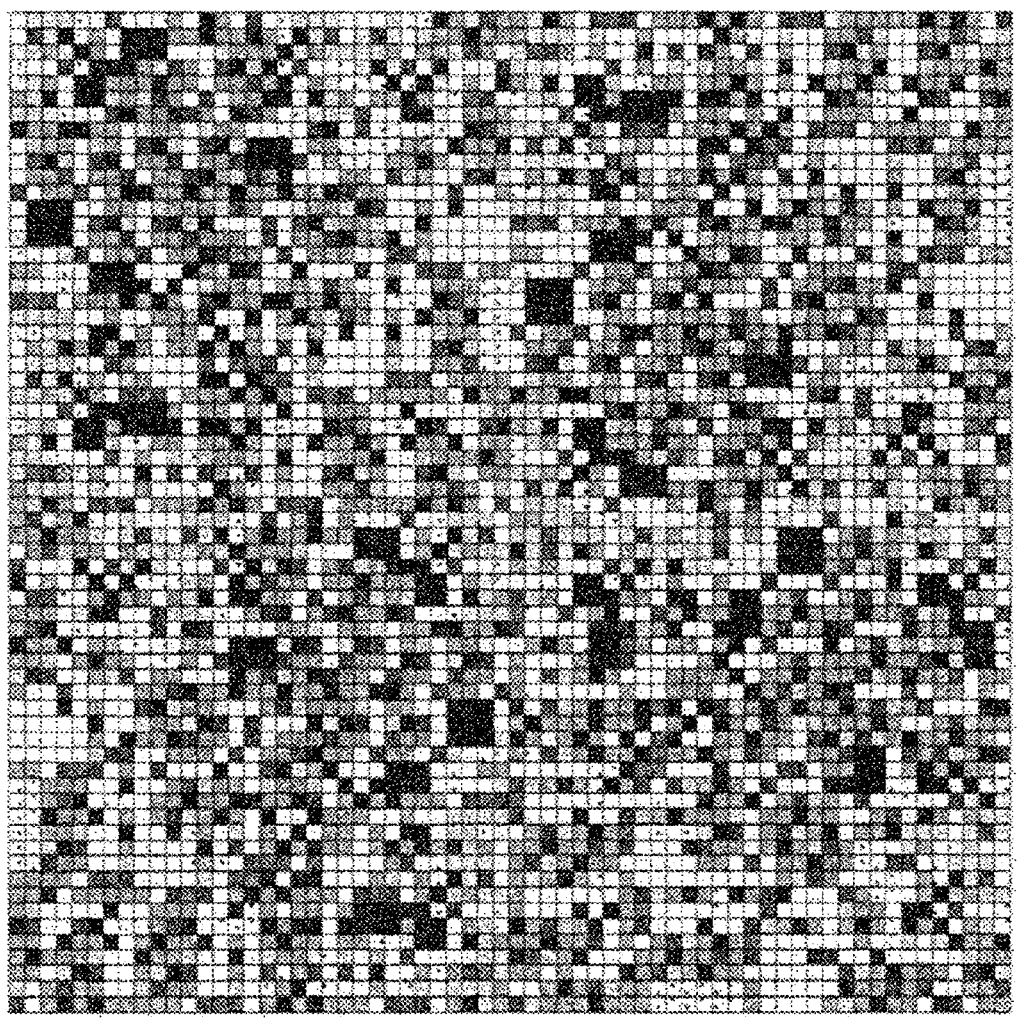
FIG. 10 is a diagram illustrating an example of the collation data.

FIG. 10 illustrates an example of the collation data obtained by cutting out data of a region having a size of 64 dots×64 dots in the collation data acquisition region 82.

In the example of the registration data illustrated in FIG. 10, it is understood that a density value of each pixel of 4096 (64×64) dots is acquired as data.

Figure 11:
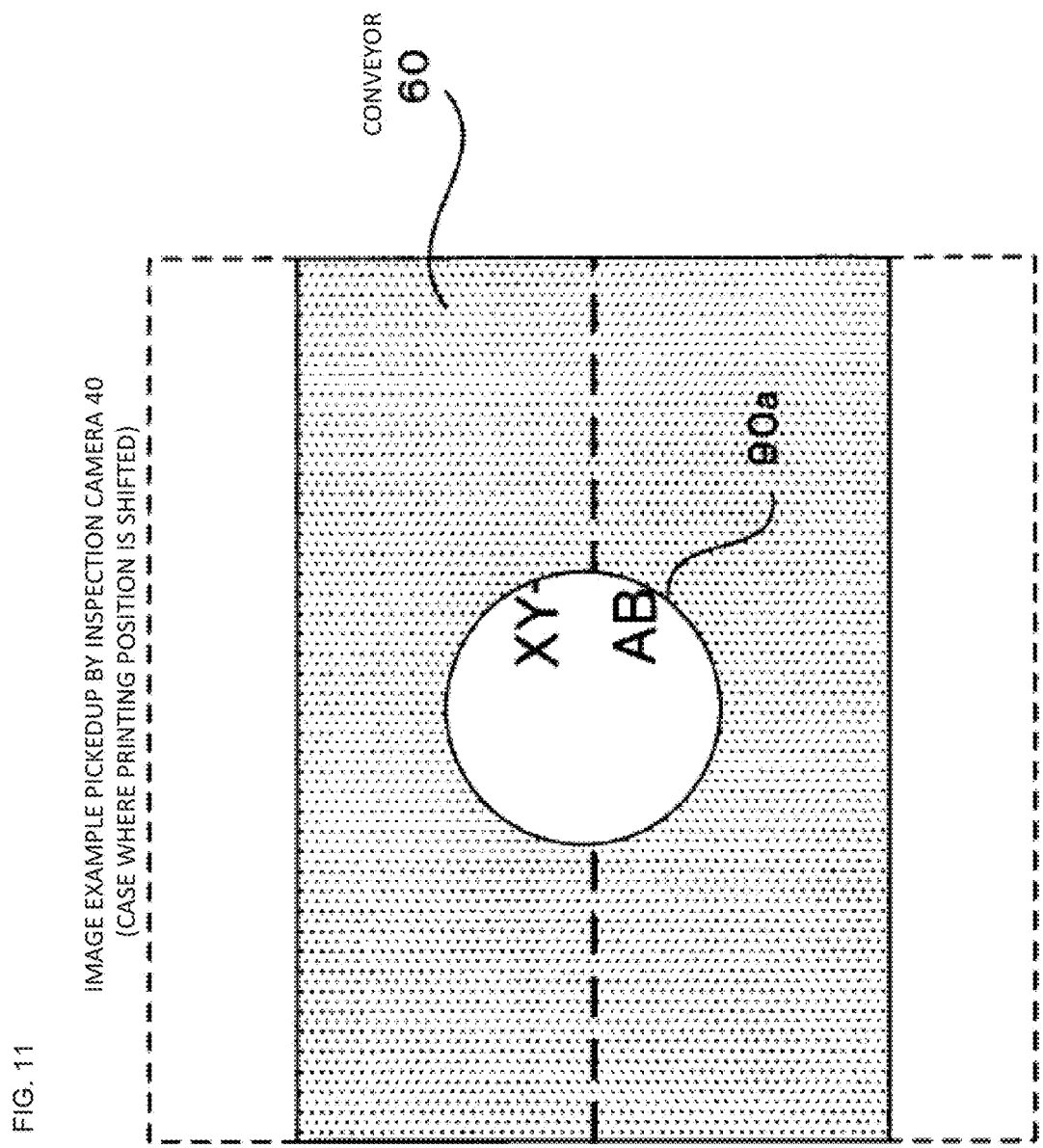
FIG. 11 is a diagram illustrating an example of an image by the inspection camera 40 in a case where printing has not been suitably performed on a tablet.

FIG. 11 illustrates an example of an image of the inspection camera 40 in a case where printing has not appropriately been performed on the tablet by printing of the print head section 50. In the example of the image illustrated in FIG. 11, a form in which an image of a tablet 90a on which printing has a print defect is picked up.

In a case where the image as illustrated in FIG. 11 is picked up by the inspection camera 40, the defective product detector 24 controls the defective product output unit 70 to output the tablet 90a as a defective product to the defective product storing box 72.

The registration data storage 23 stores registration data acquired by the registration data acquisition unit 22 as data for determining an identity of a tablet. In a case where the registration data storage 23 has available storage capacity, the registration data storage may store an entire image of the tablet on which printing has been performed, as registration data. The registration data storage 23 may preserve an entire image or at least part of the image, which is picked up by the detection camera 30 or the inspection camera 40, as data for determining an identity.

The verification unit 26 compares registration data stored in the registration data storage 23 and collation data of the same tablet, which has been acquired by the collation data acquisition unit 25, and verifies that reliability of the registration data is equal to or greater than a predetermined criterion value.

For example, in a case where a correlation value between data acquired from a region in registration data and data acquired from the corresponding region in collation data is computed and the computed correlation value satisfies a predetermined criteria, the verification unit 26 outputs a verification result that the reliability of the registration data is equal to or greater than the predetermined criterion value.

Specifically, the verification unit 26 sequentially select pieces of data having the same size as that of registration data, from pieces of collation data. The verification unit sequentially computes a correlation value between the selected data and the registration data by a normalized correlation method, so as to acquire correlation values. In a case where the maximum value of the acquired correlation values is equal to or greater than a first predetermined value and a normalized score of the maximum value of the correlation value is equal to or greater than a second predetermined value, the verification unit outputs a verification result that the reliability of this registration data is equal to or greater than the predetermined criterion value. The normalized score is obtained by dividing a value obtained by subtracting an average value from the maximum value of the correlation value by standard deviation.

The specific calculation method of the correlation value or the specific calculation method of the normalized score will be described later.

The processing section 27 performs processing based on the verification result in the verification unit 26. For example, the processing section 27 causes information of the verification result in the verification unit 26 to be stored in the registration data storage 23. Thus, the registration data storage 23 stores information of the verification result for registration data in the verification unit 26 along with the registration data.

Figure 12:
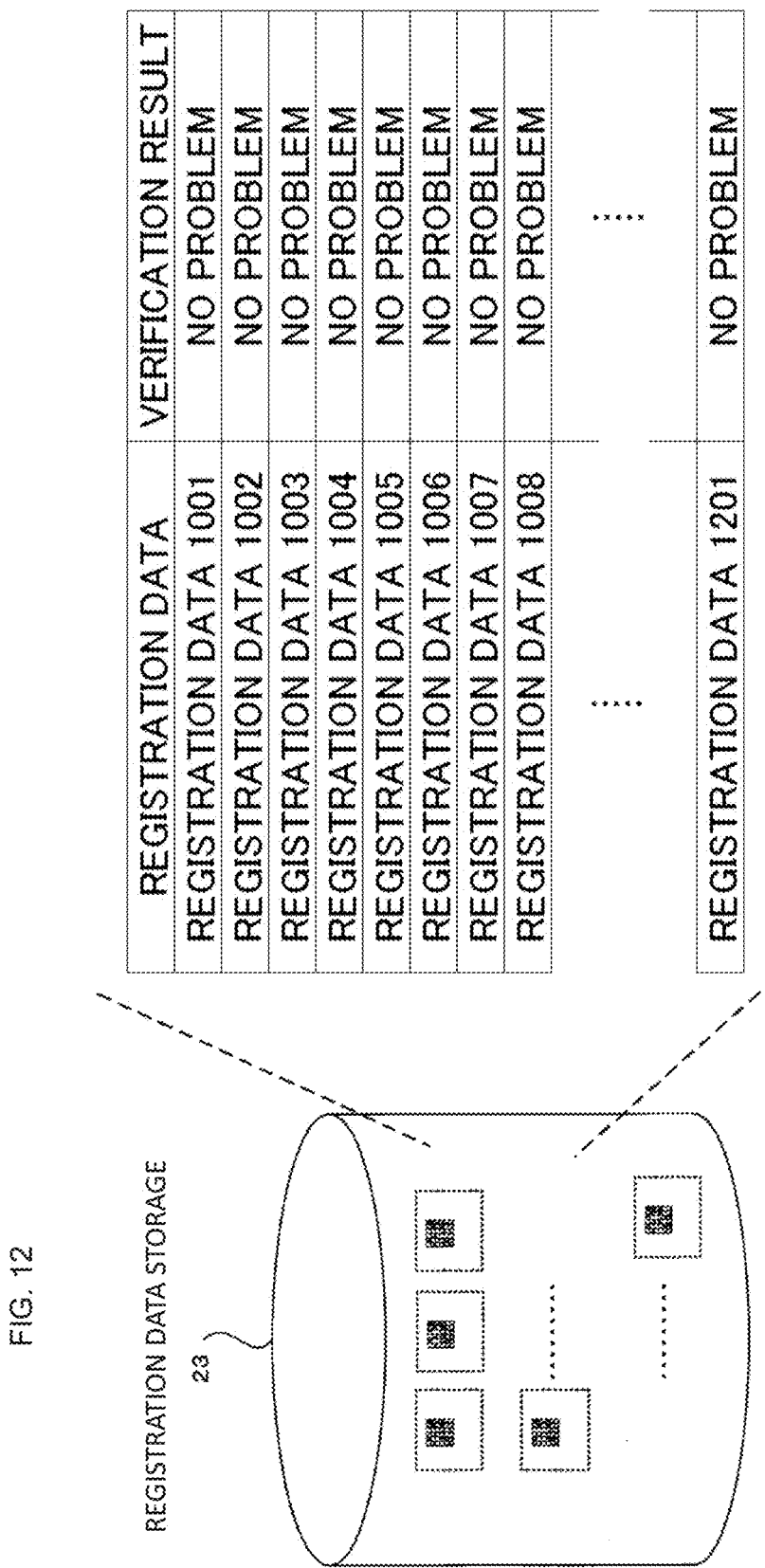
FIG. 12 is a diagram illustrating an example of data stored in a registration data storage 23.

FIG. 12 illustrates an example of data stored in the registration data storage 23. In the example illustrated in FIG. 12, it is understood that a verification result of registration data is stored along with the stored registration data. For example, in the example illustrated in FIG. 12, "registration data 1007" indicates the followings. That is, in a case where the reliability in the verification result by the verification unit 26 does not satisfy the predetermined criterion value, and collation is performed later, the tablet may be erroneously determined to be a counterfeited tablet despite being the authorized tablet.

In a case where the verification result in the verification unit 26 indicates that the reliability of the registration data is smaller than the predetermined criterion value, the processing section 27 may perform control of suspending the operation of the printing device itself.

In a case where the verification result in the verification unit 26 indicates that the reliability of the registration data is smaller than the predetermined criterion value, the processing section 27 may control the defective product output unit 70 to output this tablet to the defective product storing box 72.

Figure 13:
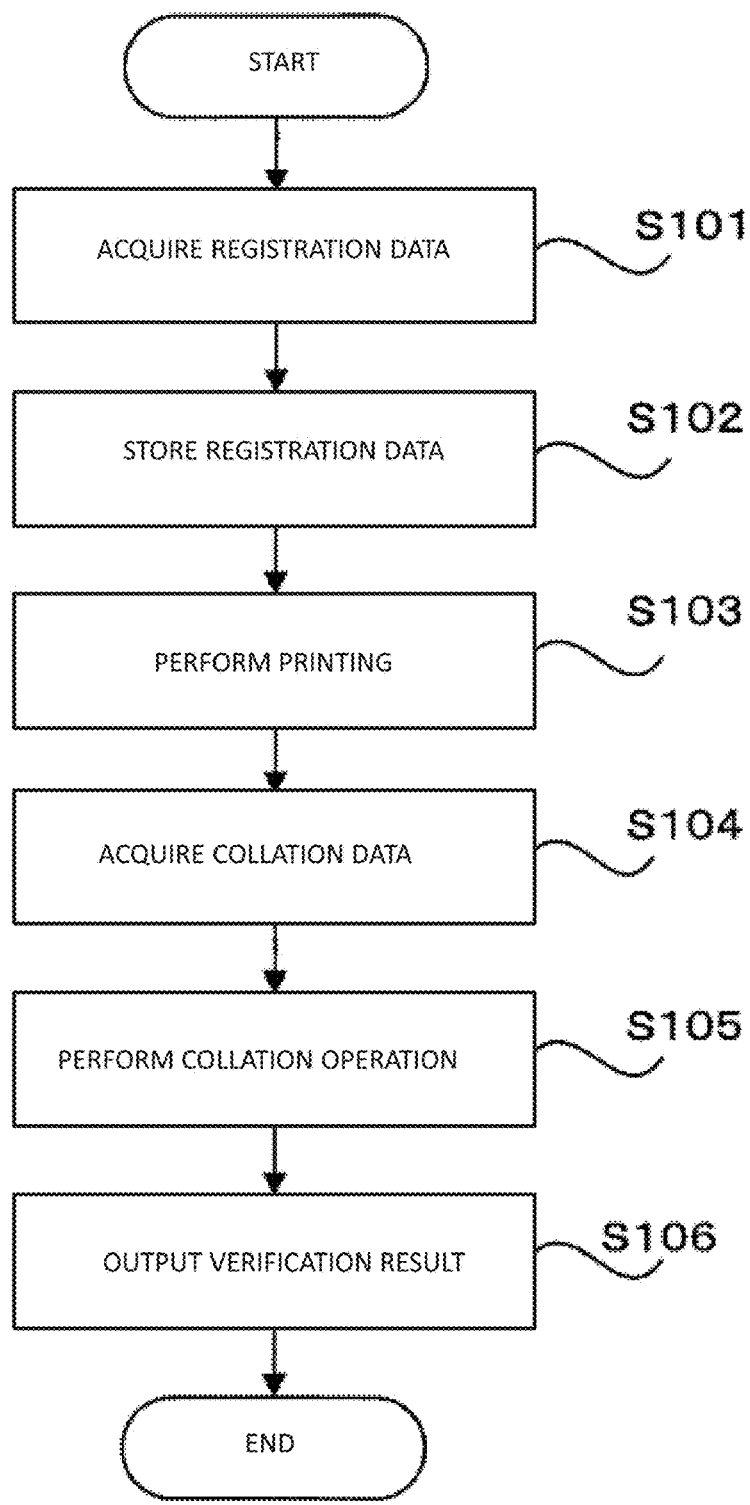
FIG. 13 is a flowchart illustrating a flow of an operation of the printing device in the first embodiment of the present invention.

Next, a flow of the operation of the printing device in the exemplary embodiment will be described with reference to the flowchart in FIG. 13.

In the printing device in the exemplary embodiment, if a tablet 90 supplied by the hopper 20 is conveyed on the conveyor 60 and then passes right under the detection camera 30, an image of the tablet 90 is picked up by the detection camera 30. The registration data acquisition unit 22 acquires registration data of 32 dots×32 dots from the image picked up by the detection camera 30 (Step S101).

The registration data acquired by the registration data acquisition unit 22 is stored in the registration data storage 23 (Step S102).

The printing controller 21 recognizes the position of the tablet 90 based on the image picked up by the detection camera 30, and performs control of the print head section 50 performing printing at a timing when the tablet 90 passes right under the print head section 50 (Step S103).

If the tablet 90 after printing is performed passes right under the inspection camera 40, an image of the tablet 90 after printing is picked up by the inspection camera 40. The collation data acquisition unit 25 acquires collation data of 64 dots×64 dots from the image picked up by the inspection camera 40 (Step S104).

The verification unit 26 reads registration data of the tablet which is the same as that of the acquired collation data, from the registration data storage 23. The verification unit 26 performs a collation operation between the registration data which has been read, and the collation data, so as to verify whether or not determination that the pieces of data are obtained from the same tablet is obtained (Step S105). That is, since the registration data and the collation data in the collation operation are acquired from the same tablet, if a computation result that the pieces of data are acquired from the same tablet is obtained in the collation operation, it is possible to determine that there is a low probability of an occurrence of erroneous determination even when a collation operation using the registration data is used later.

The verification unit 26 outputs the verification result and the processing section 27 performs processing based on the verification result in the verification unit 26 (Step S106).

Next, the specific computation method of the collation operation between registration data and collation data will be described in detail with reference to FIGS. 14 to 21.

In the following descriptions, a computation method when it is checked whether or not the reliability of registration data is equal to or greater than the predetermined reference will be described. However, the computation is performed by a similar computation method, also in a case where a collation operation between collation data acquired from an object desired to determine an identity thereof, and registration data which has been stored in advance is performed.

Firstly, FIG. 14 illustrates an example of registration data and collation data as a target of the collation operation. The collation data is data acquired from a region including a region in which the registration data has been acquired. Thus, if the collation data and the registration data are acquired from the same object, data corresponding to the registration data is necessarily included in the collation data.

Therefore, as illustrated in FIG. 15, data having the same size as that of the registration data is sequentially cut out from the collation data and correlation value computation is performed.

The correlation value computation by Expression (1) is performed when a set of pieces of registration data is set as F, the pixel value of each pixel in the registration data is set as $f_1$, the total number of pixels of the registration data (and the region cut out from the collation data) is set as N (N=32×32=1024), data of the region cut out from the collation data is set as the pixel value of each pixel in the region cut out from the collation data is set as $g_i$, the average value of pixel values of pixels in the registration data is set as $f_{AVE}$, and the average value of pixel values of pixels in the data of the region cut out from the collation data is set as $g_{AVE}$.

$$F = \{f_i\}_{i=0}^{N-1} \quad G = \{g_i\}_{i=0}^{N-1} \quad (1)$$

$$\text{correlation value} = \frac{\sum_{n=0}^{N-1} (f_n - f_{AVE})(g_n - g_{AVE})}{\sqrt{\sum_{n=0}^{N-1} (f_n - f_{AVE})^2} \sqrt{\sum_{n=0}^{N-1} (g_n - g_{AVE})^2}}$$

Figure 16:
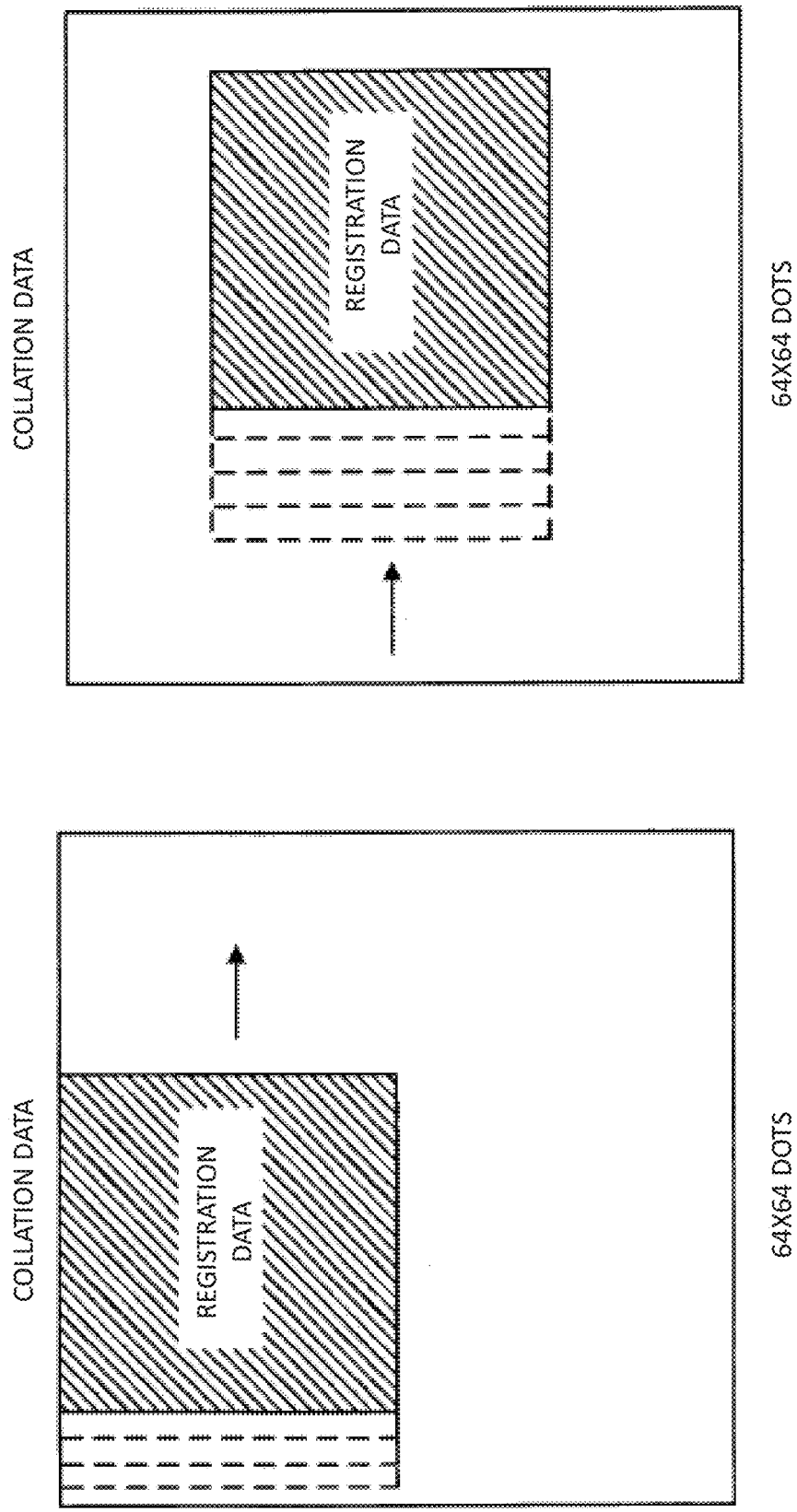
FIG. 16 is a diagram illustrating a form in which a correlation value with data cut out from the collation data is repeatedly computed while the position of the data cut out from the collation data is sequentially shifted by one dot (pixel) in an X-direction and a Y-direction.

As illustrated in FIG. 16, correlation value computation between the registration data and data cut out from the collation data repeats while the position of data cut out from the collation data is sequentially shifted by one dot (pixel) in an X-direction and a Y-direction.

As a result, 1089 ((64−32+1)×(64−32+1)) correlation values are obtained by performing a collation operation between one piece of registration data (32×32 dots) and the collation data (64×64 dots).

Figure 17:
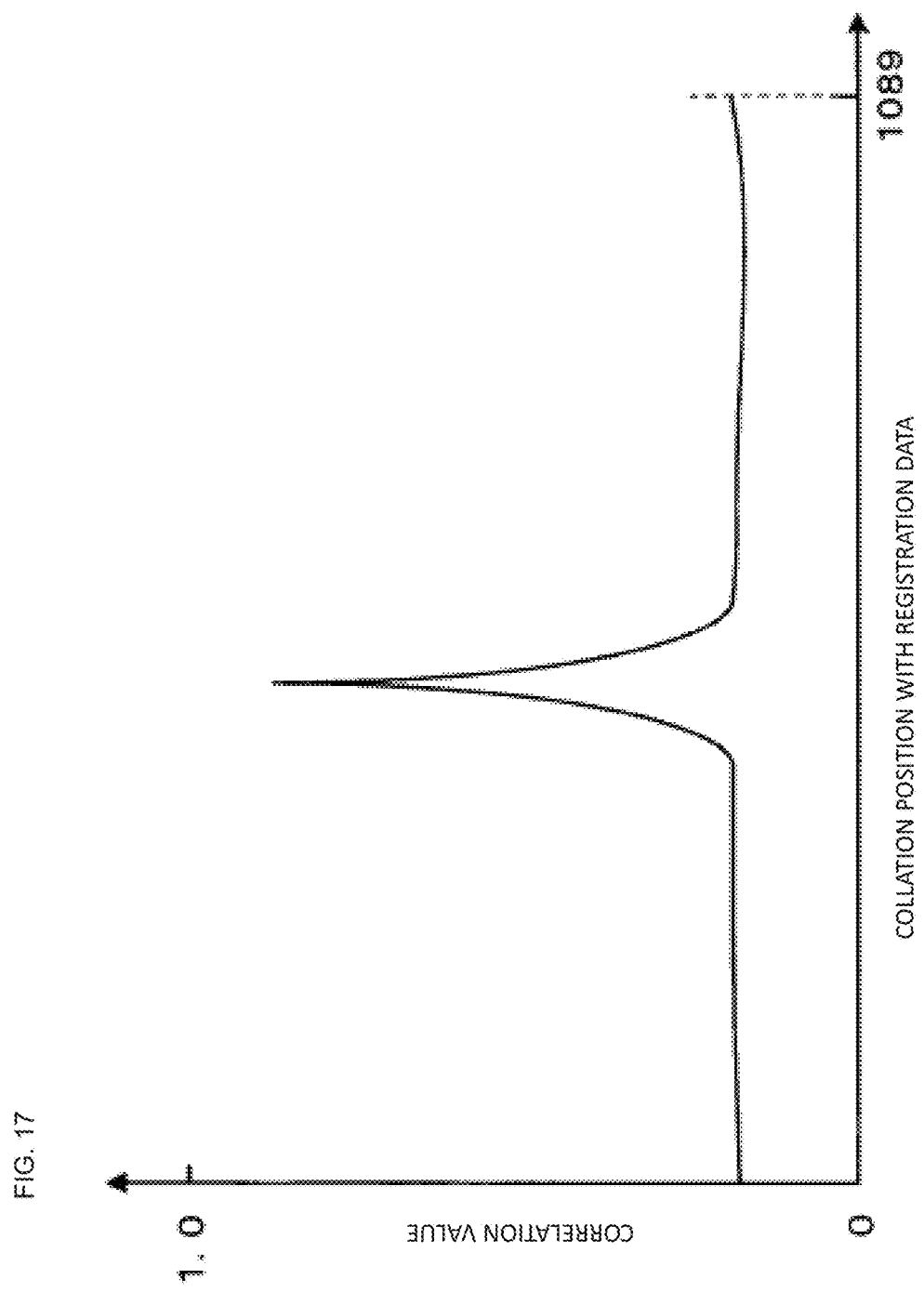
FIG. 17 is a graph illustrating 1089 correlation values obtained by the collation operation, as an example.

FIG. 17 illustrates an example of a graph of the 1089 correlation values obtained in this manner with respect to the position in the collation data, at which collation with the registration data has been performed.

In the example illustrated in FIG. 17, it is understood that the correlation value between data in the collation data at a certain position and the registration data is larger than those in other places and is close to 1.

That is, in the example illustrated in FIG. 17, it can be determined that the registration data and the collation data are acquired from the same object.

If such correlation values are obtained in the collation operation, it can be determined that the acquired registration data has reliability enough for performing the collation operation.

However, a case where acquiring normal registration data is not possible due to various factors, for example, the amount of lighting when the registration data is acquired, a problem in focus setting of the detection camera 30, and variation in distance between the detection camera 30 and the conveyor 60 by vibration.

Figure 18:
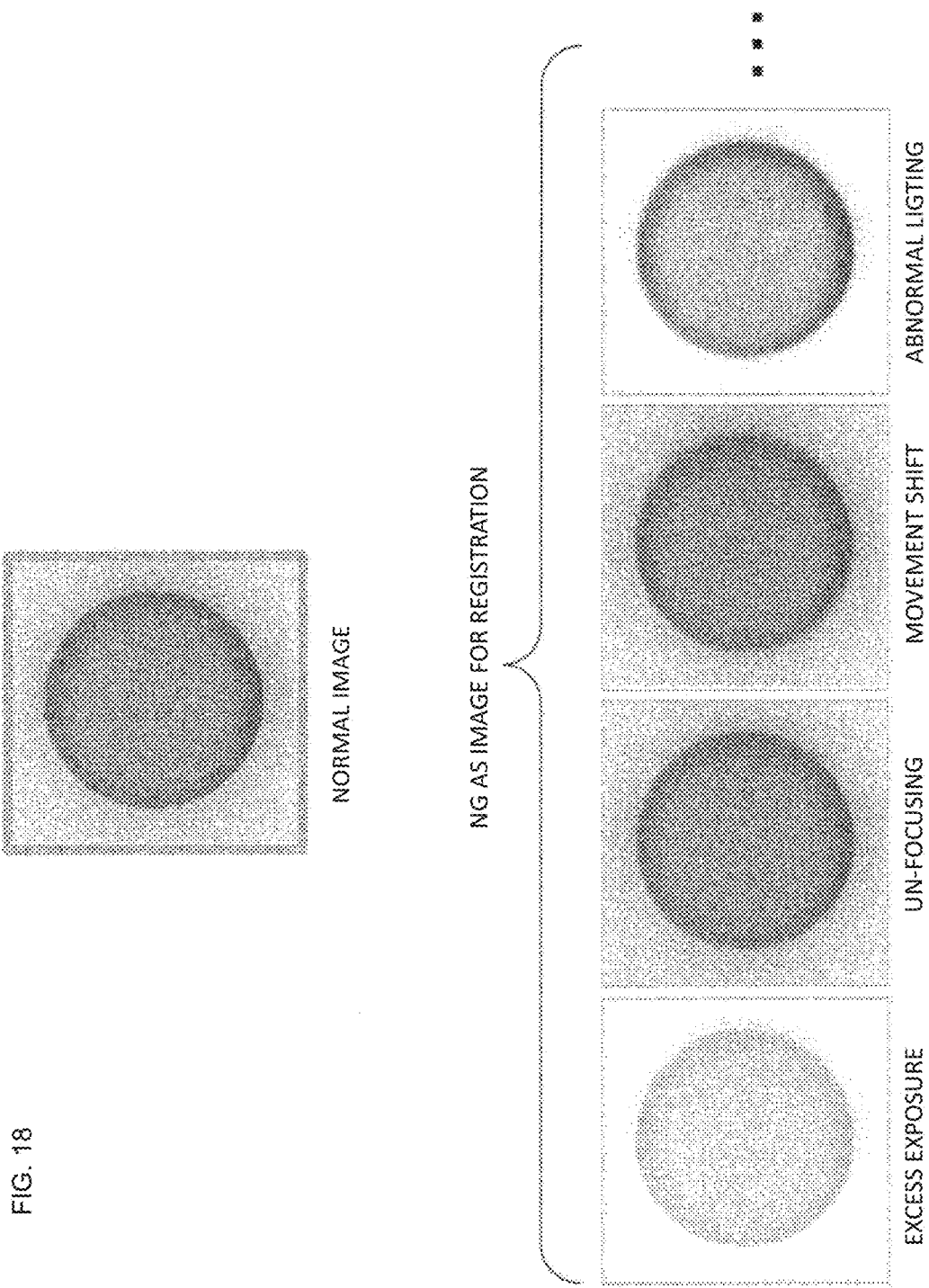
FIG. 18 is a diagram illustrating an example of an image of a tablet in a case where acquiring normal registration data is not possible.

FIG. 18 illustrates an example of an image of a tablet in such a case where acquiring normal registration data is not possible. For example, FIG. 18 illustrates an image of a tablet, which has been picked up in a case of excessive exposure, unfocusing, movement shift, abnormal lighting, and the like. In a case where the picked image of a tablet is such an image, the acquired registration data is not normal, and there is a high probability of an occurrence of erroneous determination even though the collation operation is performed.

Therefore, in the exemplary embodiment, verification of the reliability of the registration data using only the maximum value of the correlation value is not performed, but, the maximum value of the correlation value and the normalized score of the maximum value of the correlation value are computed and verification of the reliability of the registration data using the two values is performed.

The normalized score is the feature amount indicating the distribution state of the correlation value. The normalized score of the maximum value of the correlation value is calculated based on Expression (2).

Normalized score=(maximum value of correlation value−average value of correlation value)/standard deviation of correlation value (2)

The normalized score is an index indicating how far the value is from the average value of the population. Therefore, the normalized score of the maximum value of the correlation value is an index indicating how far the maximum value among the 1089 correlation values is from the average value of the correlation value.

Figure 19:
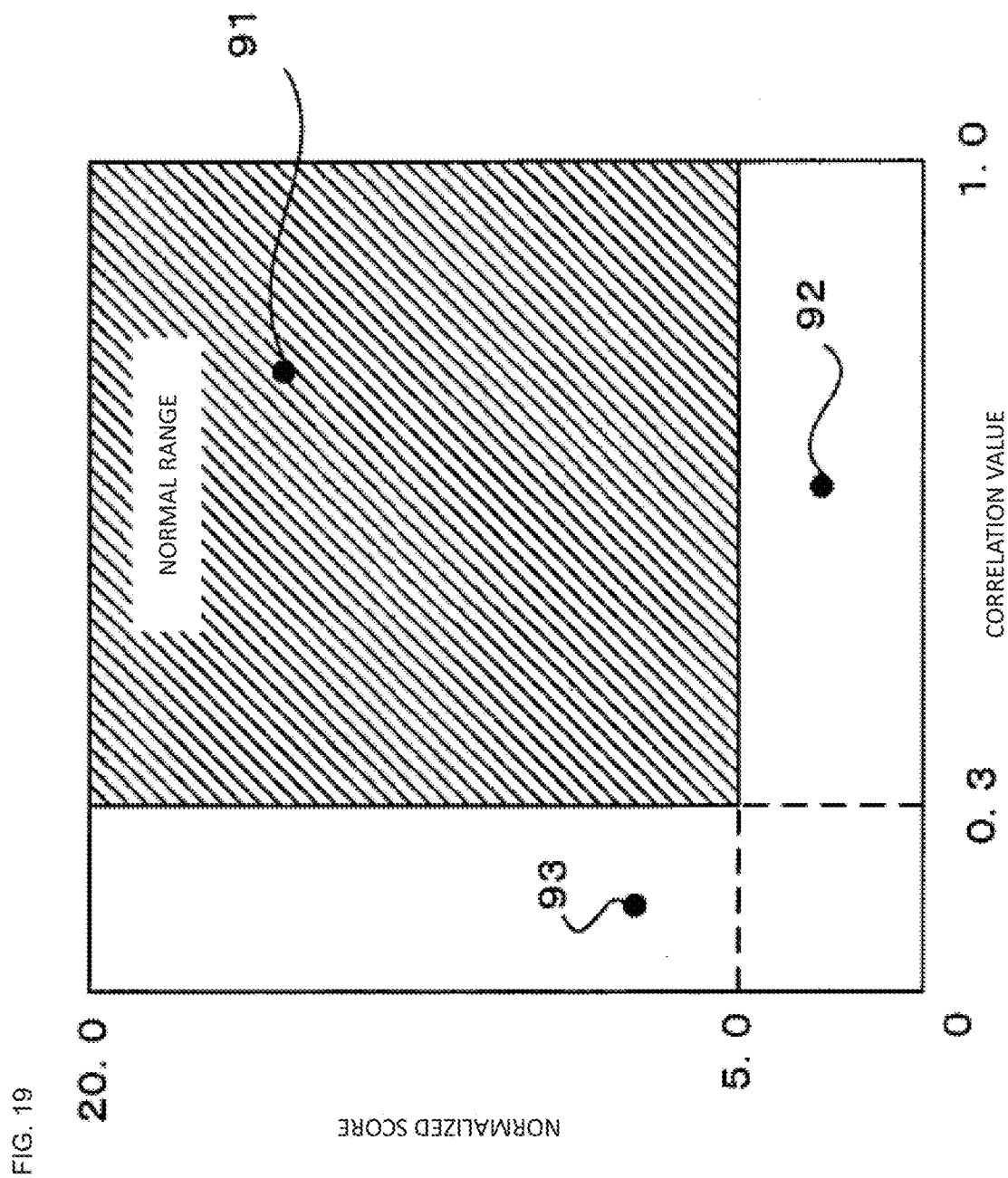
FIG. 19 is a graph illustrating an example of a range of the maximum value of a correlation value which can be used for determining that reliability of the registration data is high, and a normalized score of the maximum value of the correlation value.

In the exemplary embodiment, as illustrated in FIG. 19, in a case where the maximum value of the correlation value is equal to or greater than 0.3 and the normalized score of the maximum value of the correlation value is equal to or greater than 5.0, as an example, the verification unit 26 determines that determination with sufficiently high reliability can be performed when the collation operation is performed by using the corresponding registration data.

That is, in a case where the maximum value of the correlation value and the normalized score thereof are plotted on the graph as illustrated in FIG. 19, if the plot values are in the hatched area, the verification unit 26 determines that the registration data has high reliability. If the plot values are not in the hatched area, the verification unit determines that the registration data has low reliability.

For example, in the graph illustrated in FIG. 19, a plot value 91 indicates that the registration data has high reliability, and plot values 92 and 93 indicate that the registration data has low reliability.

Figure 20:
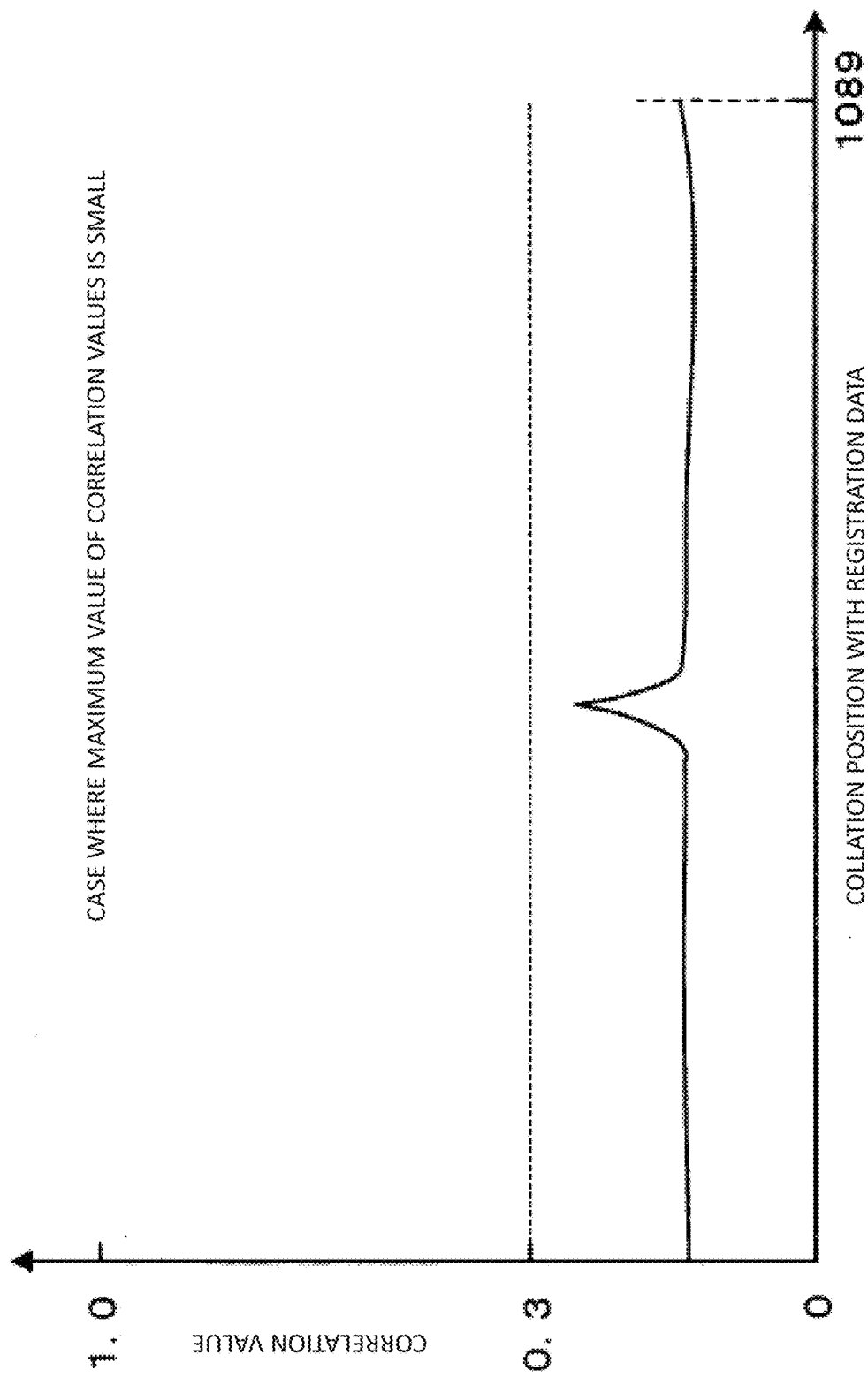
FIG. 20 is a graph illustrating an example of a correlation value in a case where the maximum value of the correlation value is small.
Figure 21:
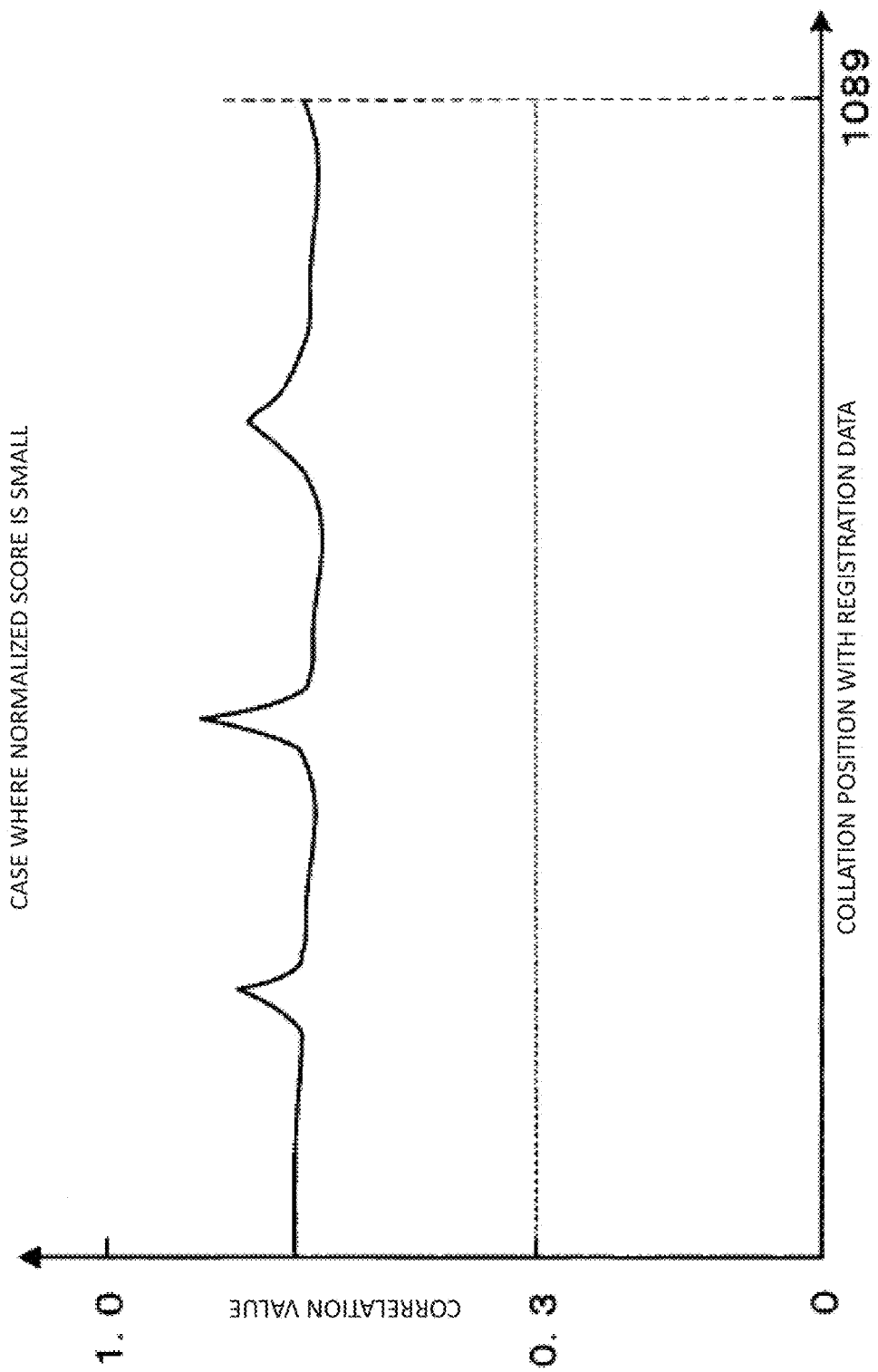
FIG. 21 is a graph illustrating an example of a correlation value in a case where the maximum value of the correlation value is equal to or greater than a criterion value, but is not normal as the registration data.

Next, FIG. 20 illustrates an example of a graph of the correlation value in a case where the maximum value of the correlation value is small. FIG. 21 illustrates an example of a graph of the correlation value in a case where the maximum value of the correlation value is equal to or greater than the criterion value, but the registration data is not normal.

In the example of the graph illustrated in FIG. 20, a case where the maximum value of the correlation value does not satisfy 0.3 of the reference and determination with high reliability even though the collation operation is performed by using the registration data is not possible is illustrated.

In the example of the graph illustrated in FIG. 21, a case where the maximum value of the correlation value is greater than 0.3 of the reference, but correlation values at almost collation positions are large, and a large correlation value is obtained even though the collation operation is performed at any collation position. Therefore, there is a high probability of performing determination with high reliability is not possible even though the collation operation is performed by using the registration data. In such a case, if the normalized score of the maximum value of the correlation value is calculated, the value is small. Thus, it is possible to accurately verify the reliability of such registration data by using the normalized score of the maximum value of the correlation value in addition to the maximum value of the correlation value.

Second Embodiment

Next, a printing device according to a second embodiment of the present invention will be described.

The configuration of the printing device in this exemplary embodiment is similar to that of the above-described printing device in the first embodiment. Thus, only a configuration different from the printing device in the first embodiment will be described.

Figure 22:
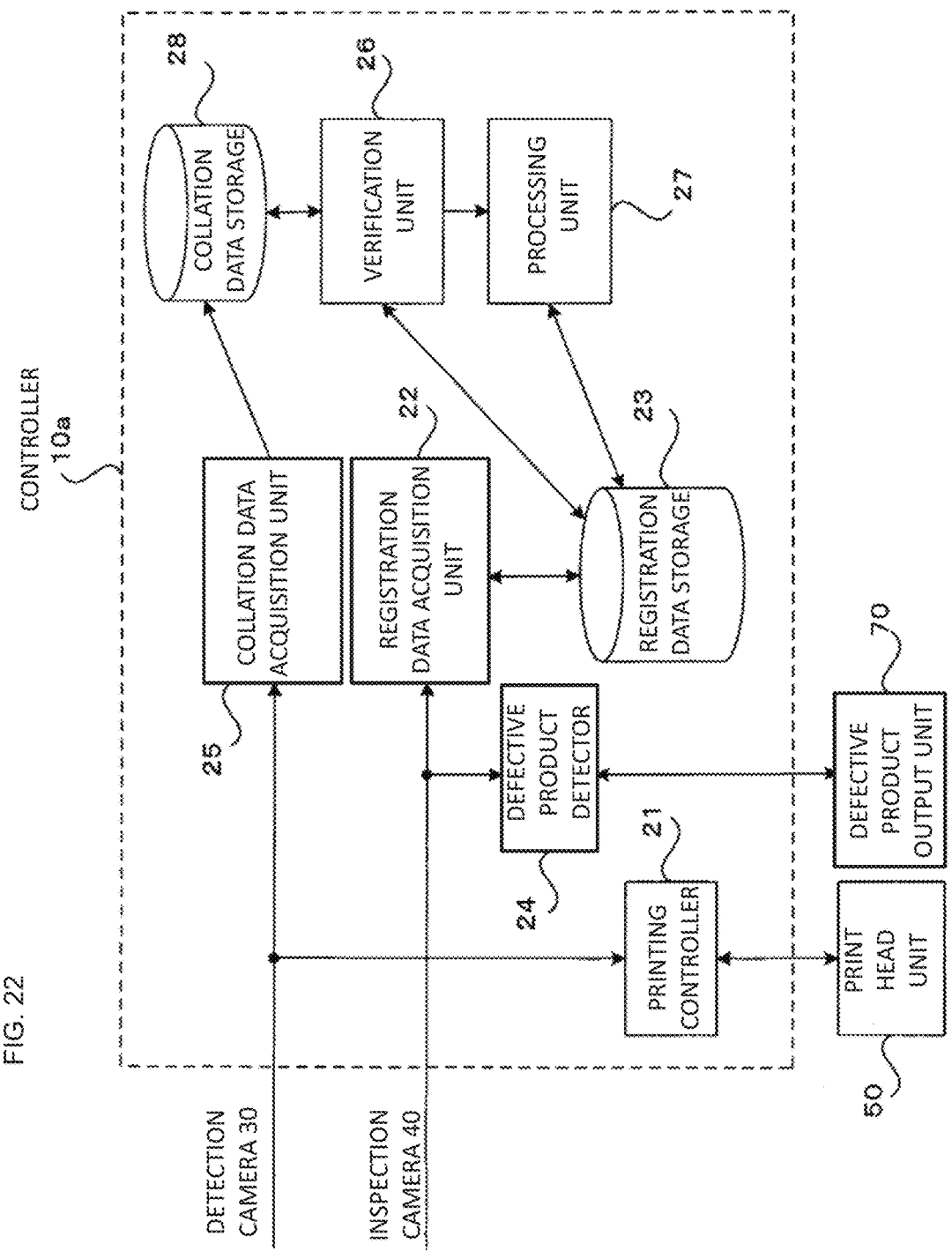
FIG. 22 is a block diagram illustrating a functional configuration of a controller 10a according to a second embodiment of the present invention.

The printing device in the exemplary embodiment has a configuration in which the controller 10 in the printing device in the first embodiment illustrated in FIG. 3 is replaced with a controller 10a as illustrated in FIG. 22.

The controller 10a in the exemplary embodiment has a configuration in which a collation data storage 28 is added to the controller 10 in the first embodiment illustrated in FIG. 3.

In the controller 10a in the exemplary embodiment, the collation data acquisition unit 25 acquires feature data indicating a feature distributed in the second region having a predetermined size on a tablet 90, from an image picked up by the detection camera 30, as collation data of 64×64 dots.

The collation data storage 28 temporarily stores the collation data acquired by the collation data acquisition unit 25.

In the controller 10a in the exemplary embodiment, the registration data acquisition unit 22 acquires feature data indicating a feature distributed in the first region having a predetermined size on the surface of a tablet 90, from an image of the tablet 90 which has been picked up by the inspection camera 40 and is subjected to printing, as registration data of 32×32 dots.

That is, in the printing device in the exemplary embodiment, collation data is acquired from an image of the detection camera 30 that picks up an image of a tablet 90 firstly and once the acquired collation data is stored. Registration data is acquired from an image of the inspection camera 40 that picks up an image of the tablet 90 after printing. Then, the reliability of the registration data is checked by using the stored collation data.

In the printing device in the exemplary embodiment, the registration data is acquired from the image including the tablet 90 after printing. Thus, in a case where the registration data storage 23 has available storage capacity, an entire image of the tablet on which printing has been performed may be stored as the registration data.

As described above, according to the two exemplary embodiments of the above-described first embodiment and this exemplary embodiment, the collation data acquisition unit 25 acquires collation data from one of an image picked up by the detection camera 30 and an image picked up by the inspection camera 40. The registration data acquisition unit 22 acquires registration data from the other image of the image picked up by the detection camera 30 and the image picked up by the inspection camera 40.

Figure 23:
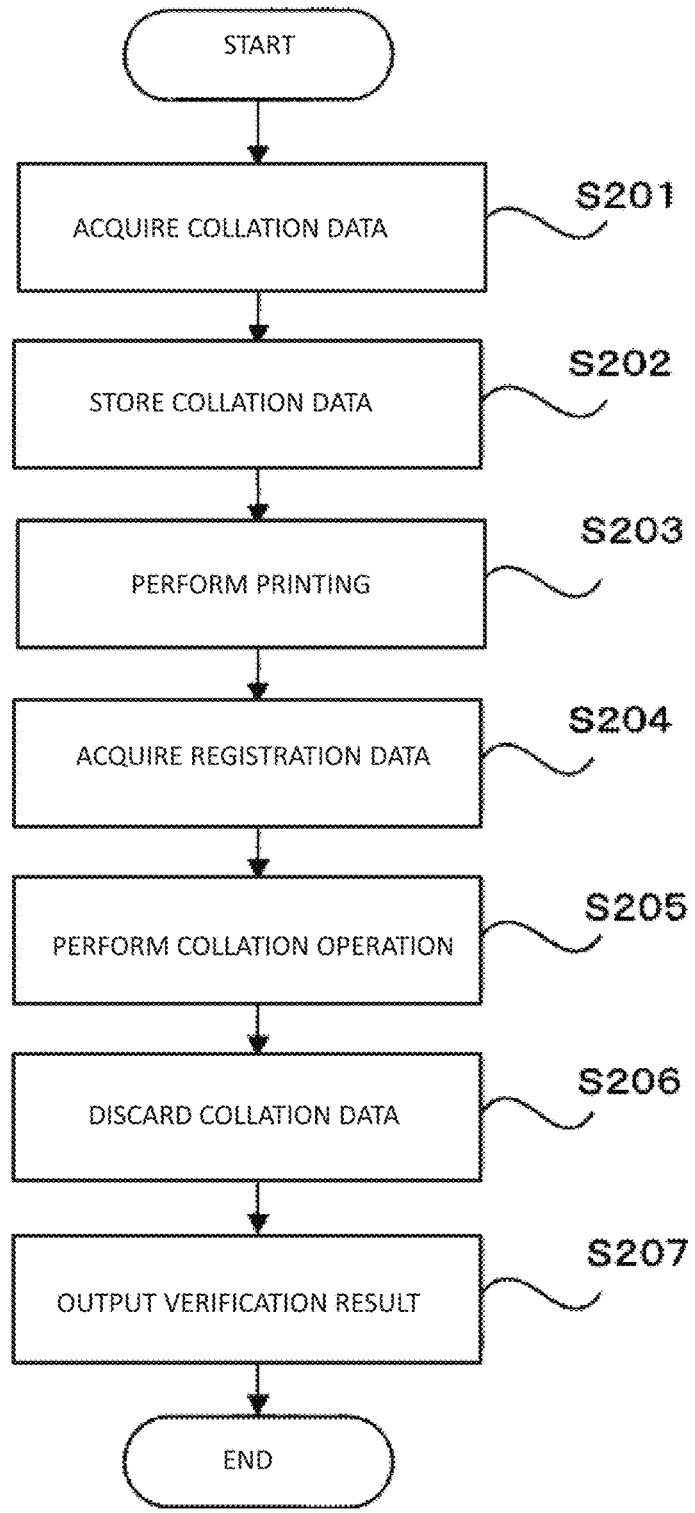
FIG. 23 is a flowchart illustrating a flow of an operation of a printing device in the second embodiment of the present invention.

Next, a flow of the operation of the printing device in the exemplary embodiment will be described with reference to the flowchart in FIG. 23.

In the printing device in the exemplary embodiment, if a tablet 90 supplied by the hopper 20 is conveyed on the conveyor 60 and then passes right under the detection camera 30, an image of the tablet 90 is picked up by the detection camera 30. The collation data acquisition unit 25 acquires collation data of 64 dots×64 dots from an image picked up by the detection camera 30 (Step S201).

The collation data acquired by the collation data acquisition unit 25 is stored in the collation data storage 28 (Step S202).

The printing controller 21 recognizes the position of the tablet 90 based on the image picked up by the detection camera 30, and performs control such that the print head section 50 performs printing at a timing at which the tablet 90 passes right under the print head section 50 (Step S203).

If the tablet 90 after printing is performed passes right under the inspection camera 40, an image of the tablet 90 after printing is picked up by the inspection camera 40. The registration data acquisition unit 22 acquires registration data of 32 dots×32 dots from the image picked up by the inspection camera 40 (Step S204).

The verification unit 26 reads registration data of the tablet which is the same as that of the acquired collation data, from the collation data storage 28. The verification unit performs a collation operation between the collation data which has been read, and the registration data, so as to verify whether or not the pieces of data are obtained from the same tablet (Step S205). That is, since the registration data and the collation data in the collation operation are acquired from the same tablet, if a computation result that the pieces of data are acquired from the same tablet is obtained in the collation operation, it is possible to determine that there is a low probability of an occurrence of erroneous determination even when a collation operation using the registration data is used later.

If the collation operation is ended, the collation data used in the collation operation is discarded (Step S206). The verification unit 26 outputs a verification result in the collation operation, and the processing section 27 performs processing based on the verification result in the verification unit 26 (Step S207).

In the printing device in the exemplary embodiment, the registration data is acquired from the image of the tablet on which printing has been performed. Thus, the processing section 27 may perform character recognition processing of information printed on the tablet after printing and store character information obtained by the character recognition processing in the registration data storage 23.

If the processing is performed in this manner, the registration data storage 23 stores the character information obtained by the character recognition processing of the verification unit 26, along with the registration data.

Figure 24:
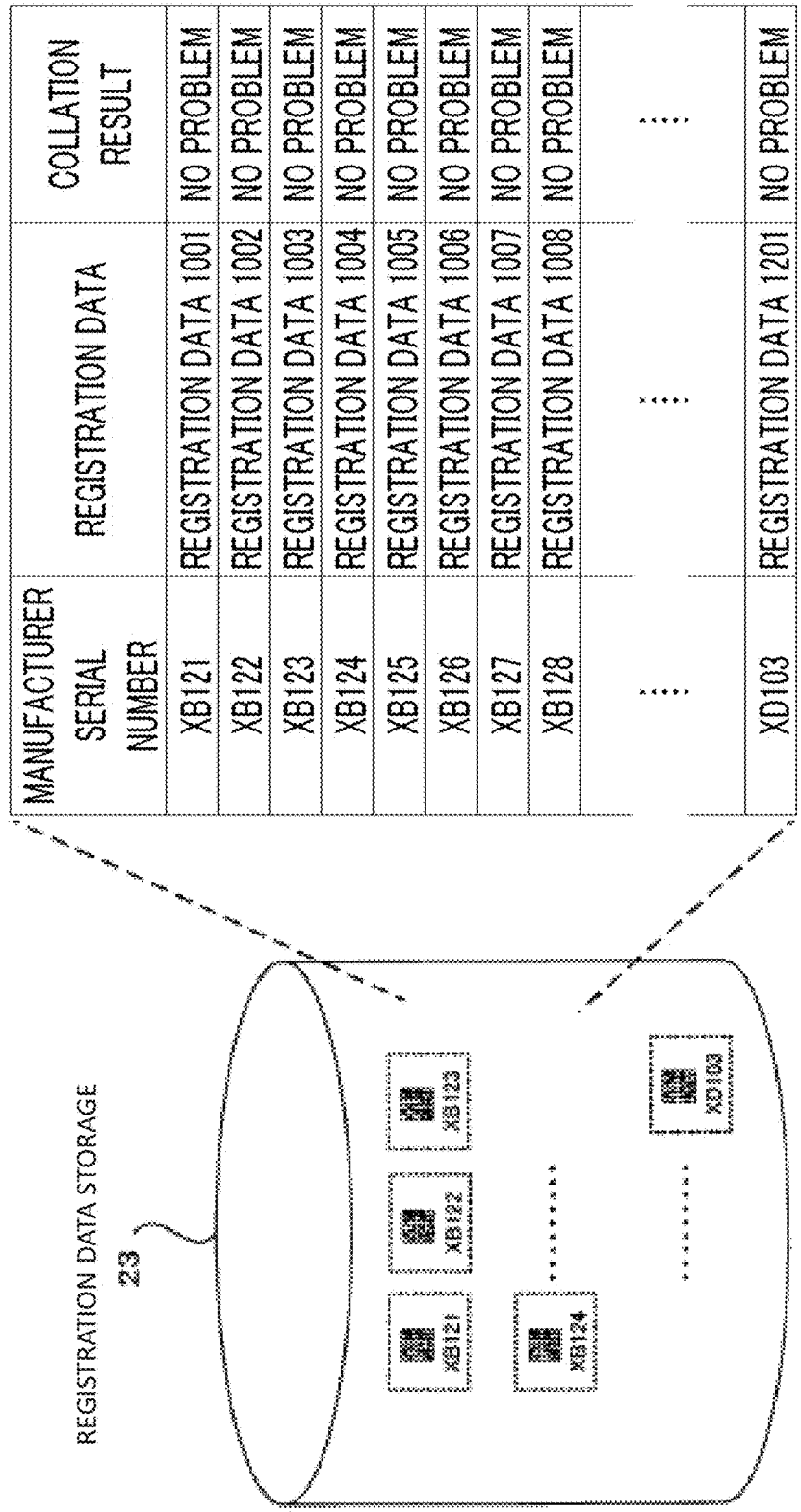
FIG. 24 is a diagram illustrating an example in which information of manufacturer serial numbers which are different for each tablet is stored along with the acquired registration data.
Figure 25:
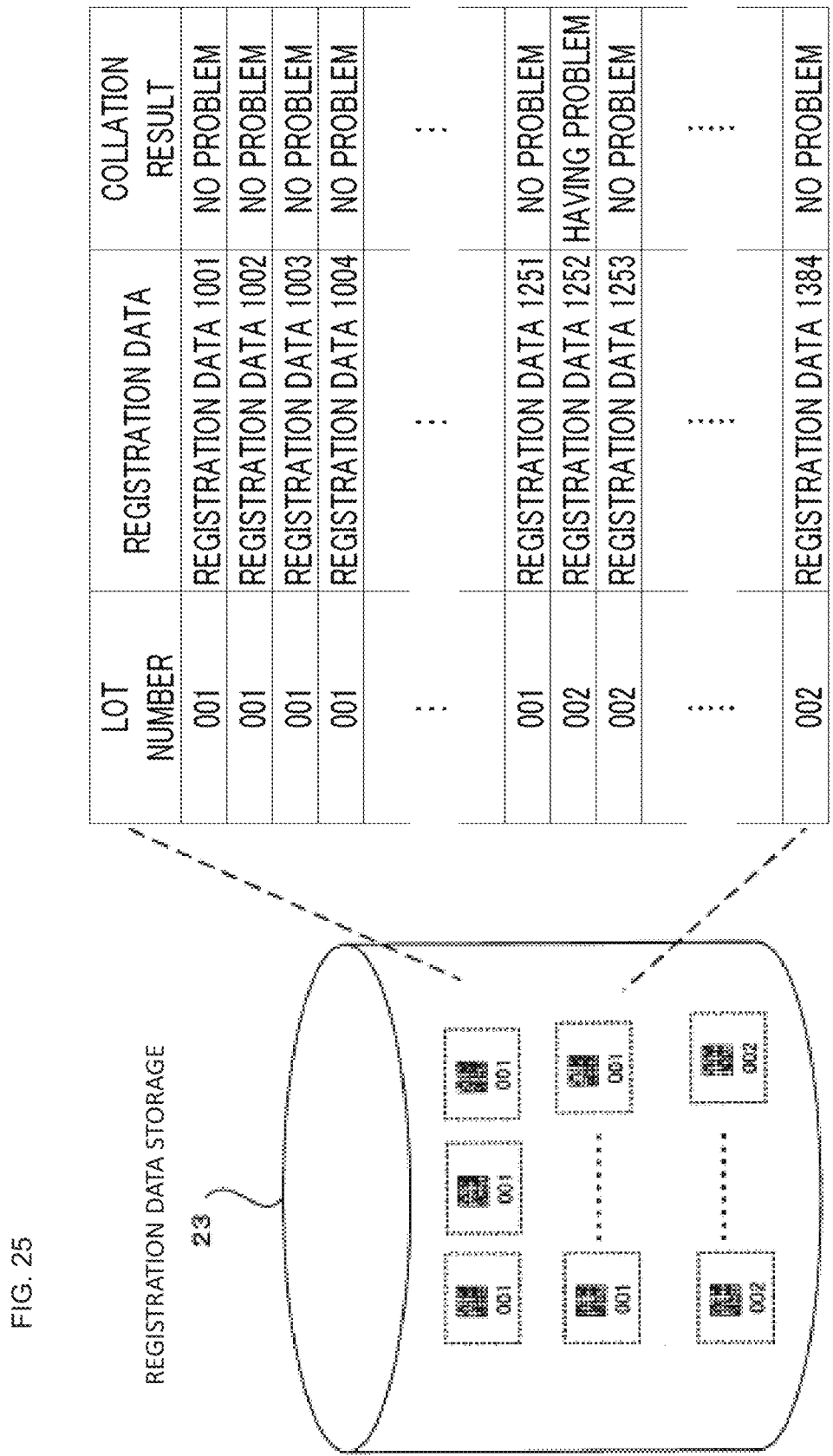
FIG. 25 is a diagram illustrating an example in which information of a lot number specifying a production unit (lot) when a tablet is manufactured is stored along with the acquired registration data.

FIGS. 24 and 25 illustrate an example of the registration data storage 23 that stores the character information along with the registration data by such processing.

In the example illustrated in FIG. 24, an example in which information of a manufacturer serial number which is different for each tablet is stored along with the acquired registration data is illustrated. As described above, if the registration data is stored along with information such as a manufacturer serial number, which can uniquely specify each tablet, collation computation may be performed only once when authenticity of a tablet on the market is determined.

For example, in a case where a manufacturer serial number which has been printed on a tablet and is set to be used when the tablet is collected from the market and authenticity of the tablet is determined is "XB125", it is possible to determine whether a tablet is authentic or counterfeit, by performing authenticity determination of the tablet only once by using registration data 1005 which is acquired from a tablet having a manufacturer serial number of "XB125" among pieces of registration data stored in the registration data storage 23.

Specifically, character recognition is performed from the image of the tablet, which has been read, by an optical character reader (OCR). Then, the characters of a manufacturer serial number printed on the tablet are extracted. Registration data stored in the registration data storage 23 is searched for by using the extracted characters, and registration data associated with the characters is extracted. Authenticity determination is performed on the image of the tablet by using the extracted registration data.

In the example illustrated in FIG. 25, an example in which information of a lot number for specifying a production unit (lot) when tablets are manufactured is stored along with the acquired registration data is illustrated. As described above, if the registration data is stored along with information such as a lot number, which can specify a lot when each tablet is manufactured, collation computation may be performed the number of times as many as the number of tablets having the lot, when authenticity of a tablet on the market is determined.

For example, in a case where a lot number which has been printed on a tablet which is collected from the market and is set to be used for determination of authenticity is "002", it is possible to determine whether a tablet is authentic or counterfeit, by performing authenticity determination of the tablet only once by using pieces of registration data 1251 to 1384 which are acquired from a tablet having a lot number of "002" among pieces of registration data stored in the registration data storage 23. That is, if the above processing is performed, it is possible to determine whether the tablet is authentic or counterfeit, without determining authenticity by using all pieces of registration data stored in the registration data storage 23.

Specifically, similar to a case of the manufacturer serial number described above, character recognition is performed from the image of the tablet, which has been read, by an optical character reader (OCR), and the characters of a lot number printed on the tablet are extracted. Registration data stored in the registration data storage 23 is searched for by using the extracted characters, and registration data associated with the characters is extracted. Authenticity determination is performed on the image of the tablet by using the extracted registration data.

Third Embodiment

Next, a printing device according to a third embodiment of the present invention will be described.

The configuration of the printing device in this exemplary embodiment is similar to that of the above-described printing device in the first embodiment. Thus, only a configuration different from the printing device in the first embodiment will be described.

In the printing device in the exemplary embodiment, reliability of registration data is improved by confirming that registration data can be normally acquired from a tablet, by using a dummy tablet (test tablet) having an appearance different from general tablets.

Figure 26:
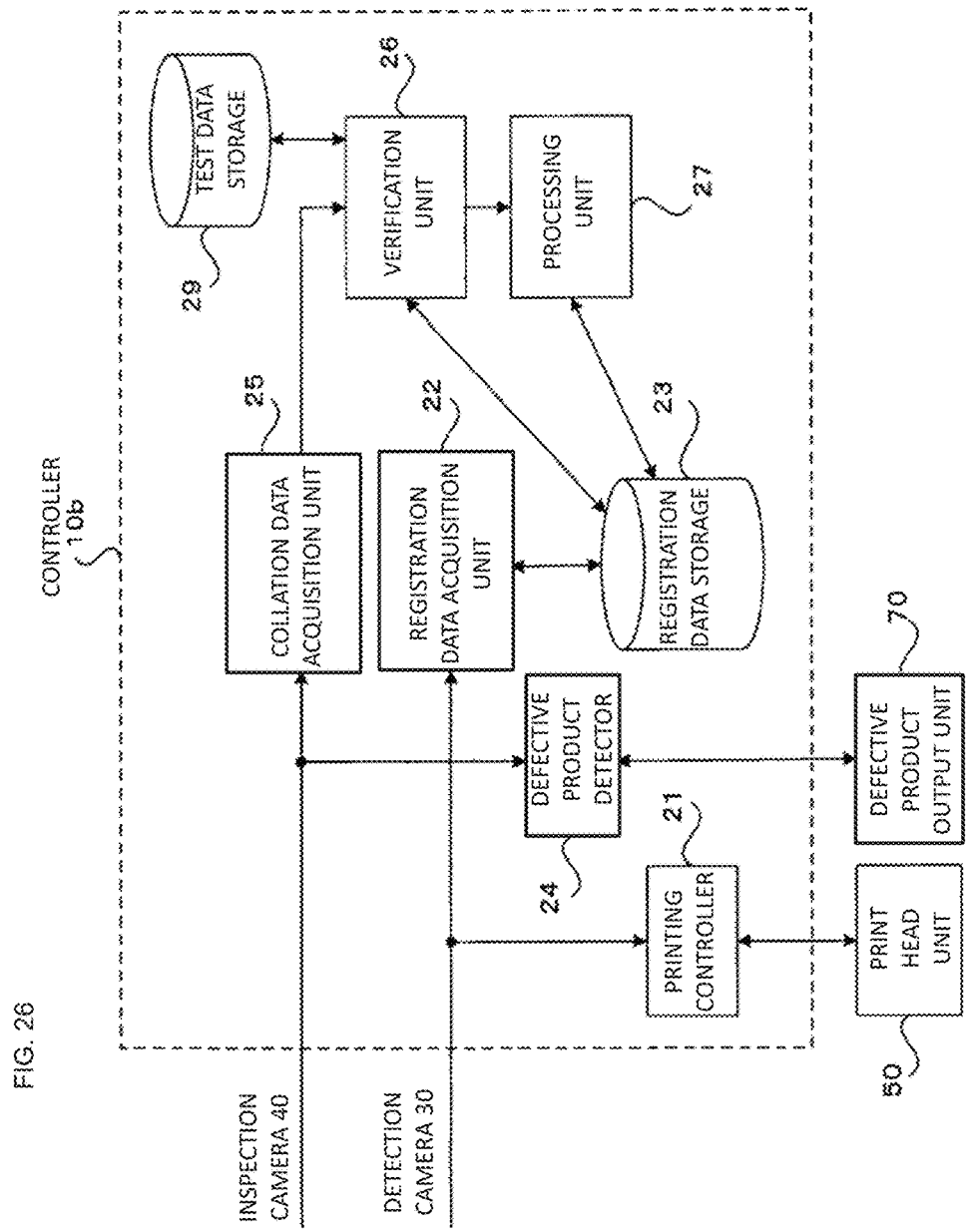
FIG. 26 is a block diagram illustrating a functional configuration of a controller 10b according to a third embodiment of the present invention.

The printing device in the exemplary embodiment has a configuration in which the controller 10 in the printing device in the first embodiment illustrated in FIG. 3 is replaced with a controller 10*b* as illustrated in FIG. 26.

The controller 10*b* in the exemplary embodiment has a configuration in which a test data storage section 29 is added to the controller 10 in the first embodiment illustrated in FIG. 3.

Figure 27:
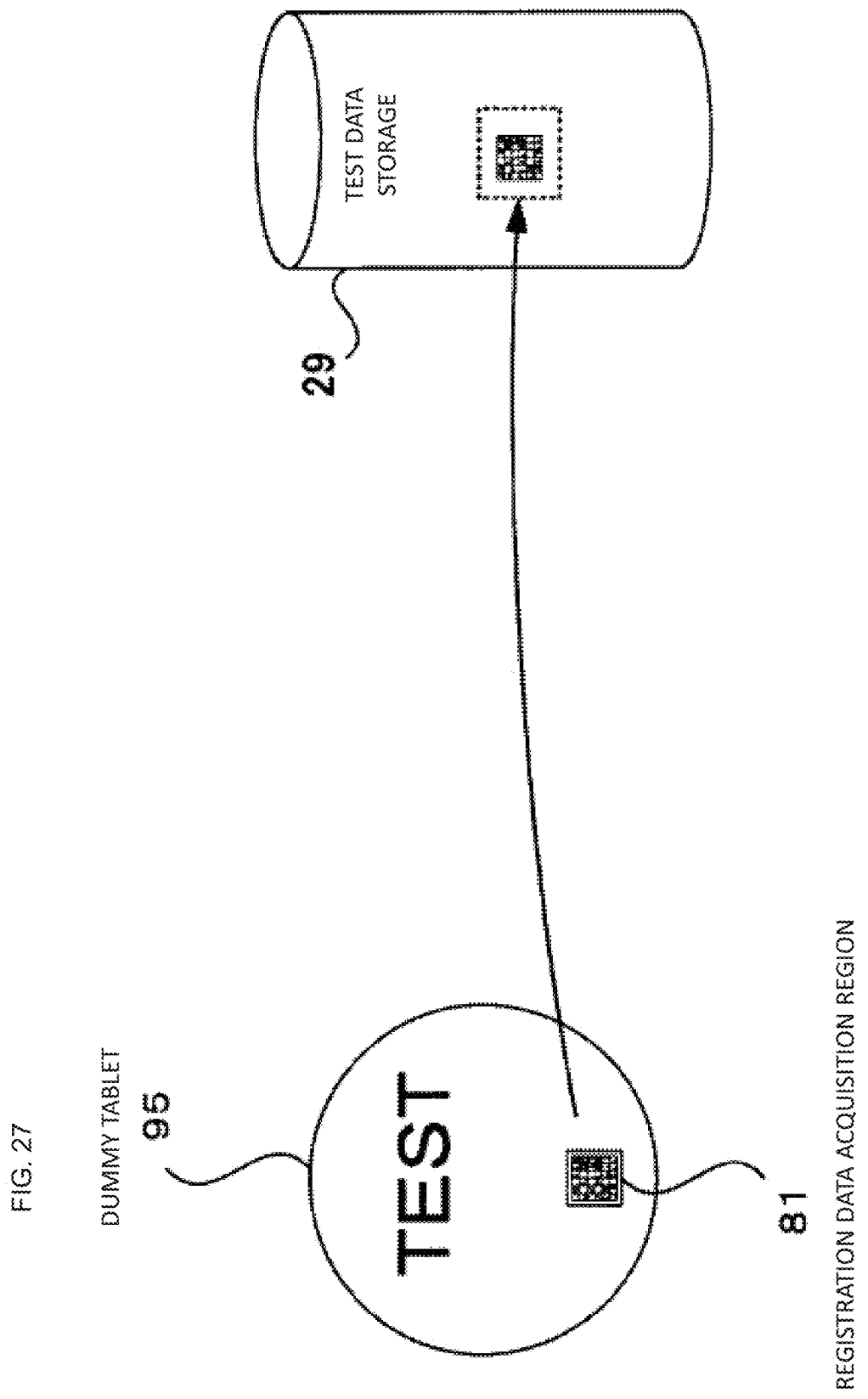
FIG. 27 is a diagram illustrating test data stored in a test data storage section 29.

As illustrated in FIG. 27, the test data storage section 29 stores registration data of 32×32 dots which has been acquired from the registration data acquisition region 81 in a dummy tablet 95 on which characters of "TEST" are printed in advance, as test data.

Here, for simple descriptions, a case where registration data of one dummy tablet is stored in the test data storage section 29 will be described. However, in practice, plural pieces of registration data acquired from dummy tablets may be stored as the test data.

Next, an operation of the printing device in the exemplary embodiment will be described with reference to FIG. 28.

Figure 28:
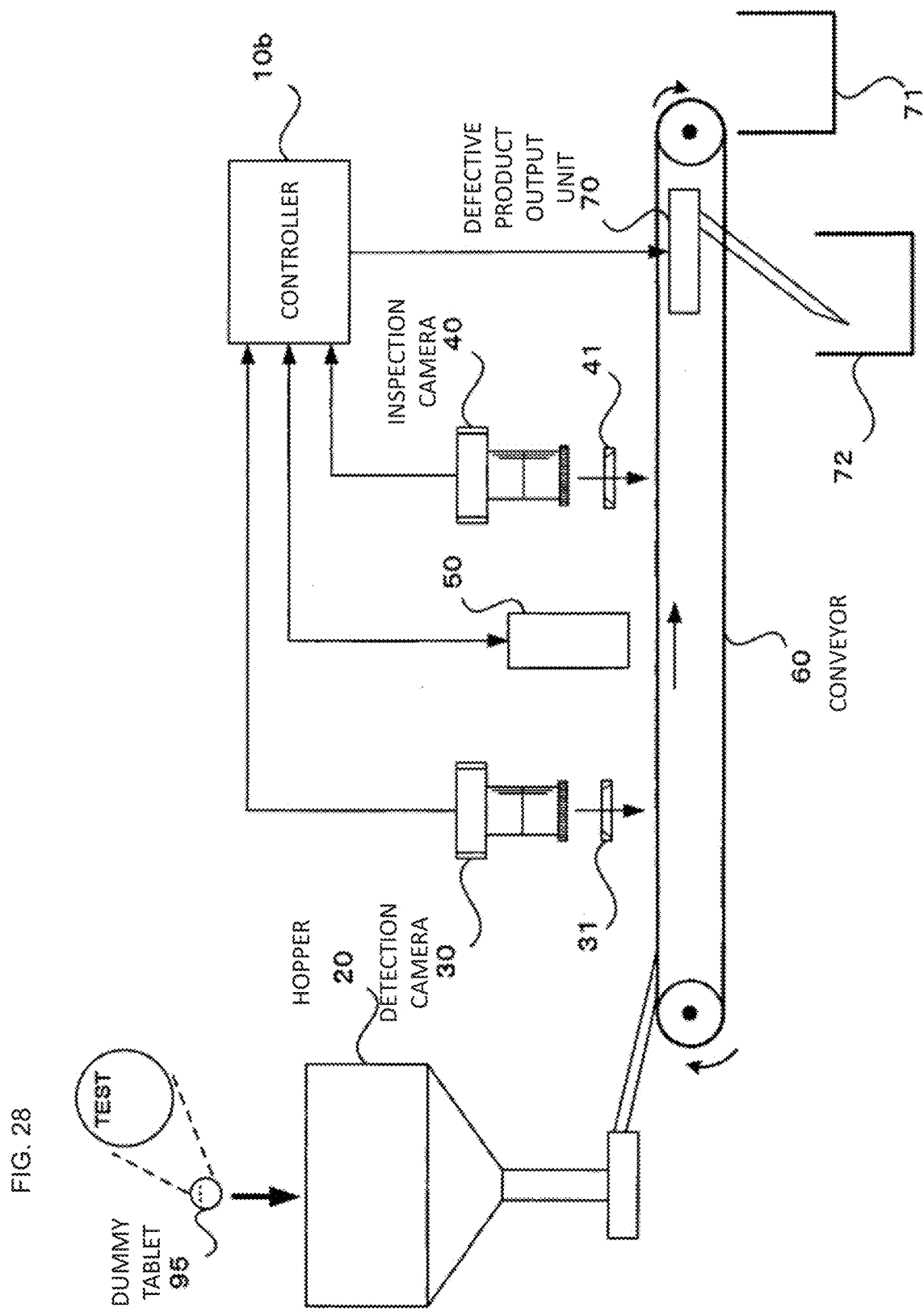
FIG. 28 is a diagram illustrating an operation of a printing device in the third embodiment of the present invention.

Firstly, as illustrated in FIG. 28, one or more dummy tablets 95 is put into the hopper 20 when printing on a tablet starts. The dummy tablet 95 is conveyed on the conveyor 60 and an image thereof is picked up by the detection camera 30.

If the printing controller 21 checks that characters of "TEST" are printed on a tablet in the image picked up by the detection camera 30, the printing controller 21 determines the tablet to be the dummy tablet 95 and then suspends a printing operation of the print head section 50.

Therefore, the dummy tablet 95 passes under the print head section 50 without performing printing, and then an image thereof is picked up by the inspection camera 40.

Then, the collation data acquisition unit 25 acquires collation data from the image of a dummy tablet 95 in a case where the tablet in the image acquired by the inspection camera 40 is the dummy tablet.

In a case where the tablet in the image acquired by the inspection camera 40 is the dummy tablet, the verification unit 26 compares test data stored in the test data storage section 29 and the acquired collation data, and thus verifies that the printing device normally operates.

Specifically, the verification unit 26 performs collation computation of the collation data acquired from the dummy tablet and each piece of test data stored in the test data storage section 29. If the collation data acquired from the dummy tablet coincides with any piece of test data on which the collation computation has been performed, the verification unit determines that the device normally operates.

Figure 29:
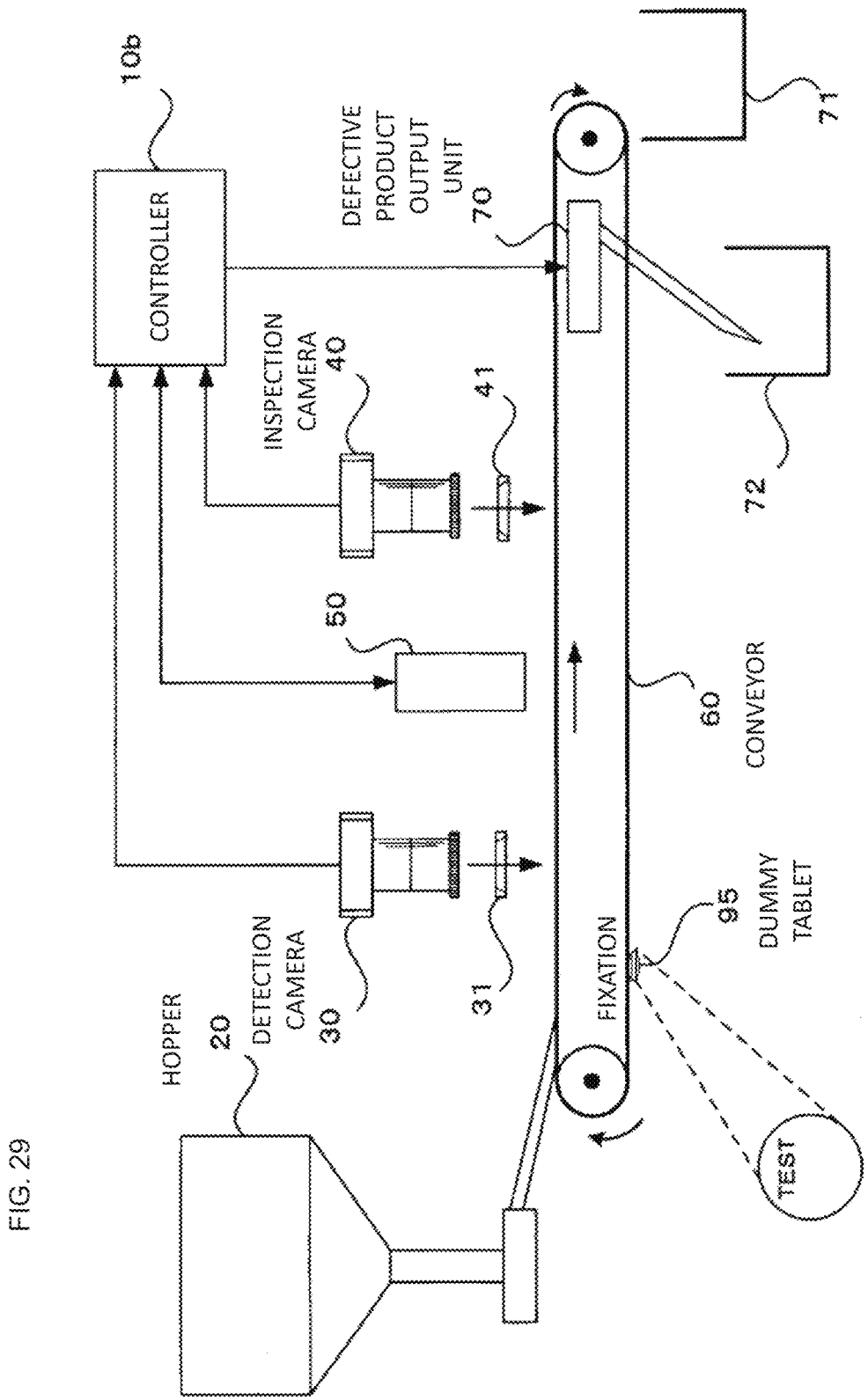
FIG. 29 is a diagram illustrating a printing device in which a dummy tablet 95 is fixed on a conveyor 60.

Not the dummy tablet 95 is put from the hopper 20 and operation checking of the device is performed, but the dummy tablet 95 may be fixed on the conveyor 60 for conveying tablets, as illustrated in FIG. 29.

As described above, since the dummy tablet 95 is fixed on the conveyor 60, an image of the dummy tablet 95 is regularly picked up by the detection camera 30 and the inspection camera 40 and thus an operation checking operation is performed.

Figure 30:
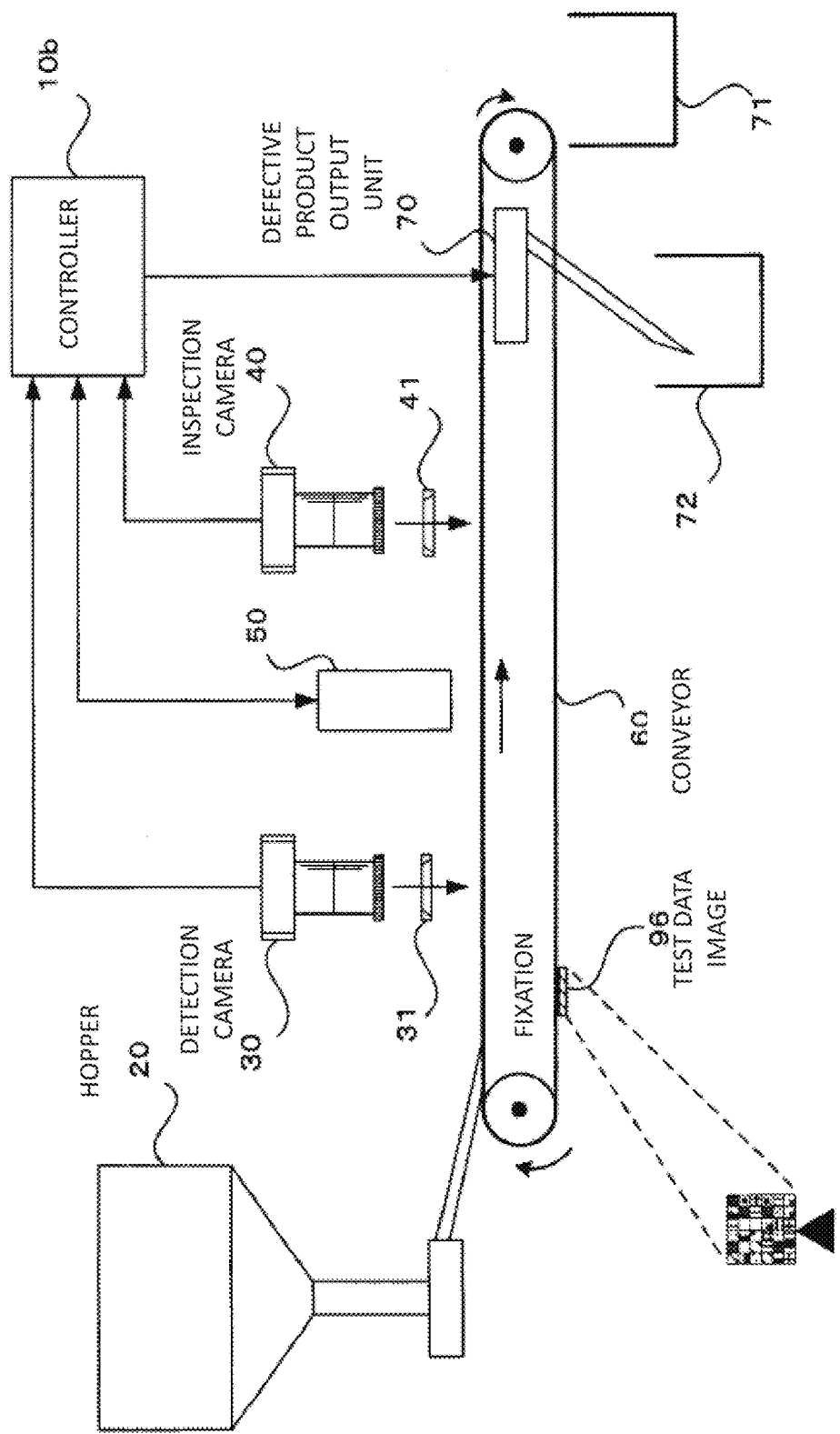
FIG. 30 is a diagram illustrating a printing device in which a test data image 96 is fixed on the conveyor 60.

Not the dummy tablet 95 is fixed on the conveyor 60, but an image of collation data acquired from the dummy tablet 95 may be fixed on the conveyor 60, as test data image 96, as illustrated in FIG. 30.

For example, a specific mark such as a triangle mark, which allows detection that the image is the test data image 96 is included in the test data image 96.

Therefore, in a case where an image pattern of the test data image 96 is included in the image acquired by the inspection camera 40, the collation data acquisition unit 25 in the printing device in the exemplary embodiment acquires the image pattern of the test data image 96 as collation data.

The verification unit 26 compares the test data stored in the test data storage section 29 and the acquired collation data, and verifies whether or not the printing device normally operates.

Fourth Embodiment

Next, a printing device according to a fourth embodiment of the present invention will be described.

The configuration of the printing device in the exemplary embodiment is similar to the above-described printing devices in the first to third embodiments. Thus, only a configuration which is different from the printing devices in the exemplary embodiments will be described.

In the printing device in the exemplary embodiment, only a method of determining the position of the registration data acquisition region 81 which is a region when the registration data acquisition unit 22 acquires registration data is different. Other configurations are similar to those in other exemplary embodiments.

In the exemplary embodiment, in a case where the registration data acquisition unit 22 acquires registration data from an image of a tablet after printing, the registration data acquisition unit 22 determines the position of the registration data acquisition region 81 for acquiring the registration data, based on the position defined by the position of the printing pattern.

Here, in an object such as a circular tablet, which has an inclining surface, an appearance of a shadow (density of shadow) by a surface light source such as the ring lighting unit 31 or 41 and by fine unevenness varies largely depending on the place.

Figure 31A:
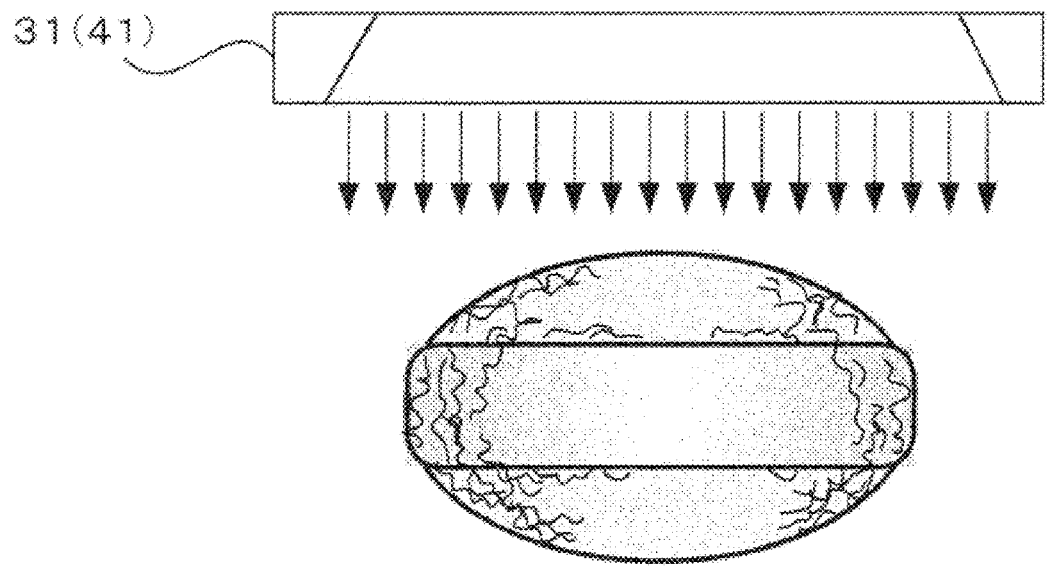
FIGS. 31A and 31B are diagrams illustrating a form in a case where a circular tablet is irradiated with light from a ring lighting unit 31 (41)

For example, in a case where a circular tablet as illustrated in FIG. 31(A) is irradiated with light from the ring lighting unit 31 (41), the shadow at the central portion of the tablet appears weakly, but the shadow at the peripheral portion appears strongly. That is, the information quantity of a random pattern at the peripheral portion is greater than that at the central portion.

Figure 31B:
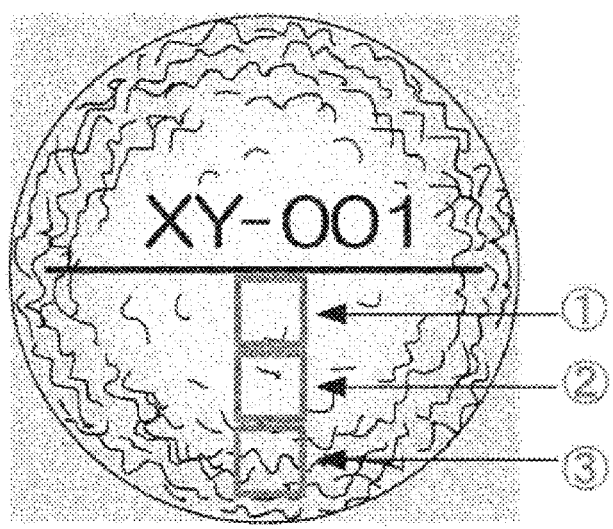

For example, as in the example illustrated in FIG. 31(B), it is understood that the information quantity of the random pattern increases as much as going from the central portion of the tablets toward the peripheral portion thereof.

Therefore, in a case where registration data is acquired from an object such as a circular tablet, it is desired that the position of the registration data acquisition region 81 is set to be close to the peripheral portion of the object as much as possible.

However, in a case where characters and the like are printed on an object and the position of the registration data acquisition region 81 is defined based on the characters and the like, there is a problem in a case where printing deviation and the like occur.

In a case where printing is performed on an object such as a tablet, since the printing is performed on the object in the process of being conveyed, the printing pattern is not uniformly provided at a predetermined position with respect to the shape of the object. Therefore, in a case where the position of the registration data acquisition region 81 is defined based on the printing pattern, if printing deviation occurs, normal registration data can not be acquired in some cases.

For example, the examples illustrated in FIGS. 32A to 32E show how the acquisition region of registration data changes if printing deviation occurs in a case where characters of "XY-001" and a horizontal line are printed on a circular tablet.

FIGS. 32A to 32E illustrate cases where the vertical bisector of the horizontal line is virtually drawn on the tablet, and a position at a predetermined distance from the horizontal line is defined as the center of the registration data acquisition region.

In such a case, as illustrated in FIG. 32A, in a case where the printing pattern is normally printed, the registration data acquisition region is set at the appropriate position.

As illustrated in FIG. 32C, even in a case where the orientation of the printing pattern is slightly inclined, the registration data acquisition region is set at the appropriate position.

However, in a case where the printing pattern is printed in a state of being shifted from the center as illustrated in FIGS. 32B and 32D, the registration data acquisition region is not set at the appropriate position.

As illustrated in FIG. 32E, in a case where the printing pattern is printed in a state of being largely shifted from the center, the registration data acquisition region is not set at a position at which registration data can be normally acquired, and the registration data acquisition region is set in a region on the outside of the outer shape of the tablet.

The registration data acquisition unit 22 in the printing device in the exemplary embodiment determines the position of the registration data acquisition region 81 for acquiring registration data, based on the position defined by both the outer shape of the tablet and the position of the printing pattern (print information) printed on the tablet.

Figure 33:
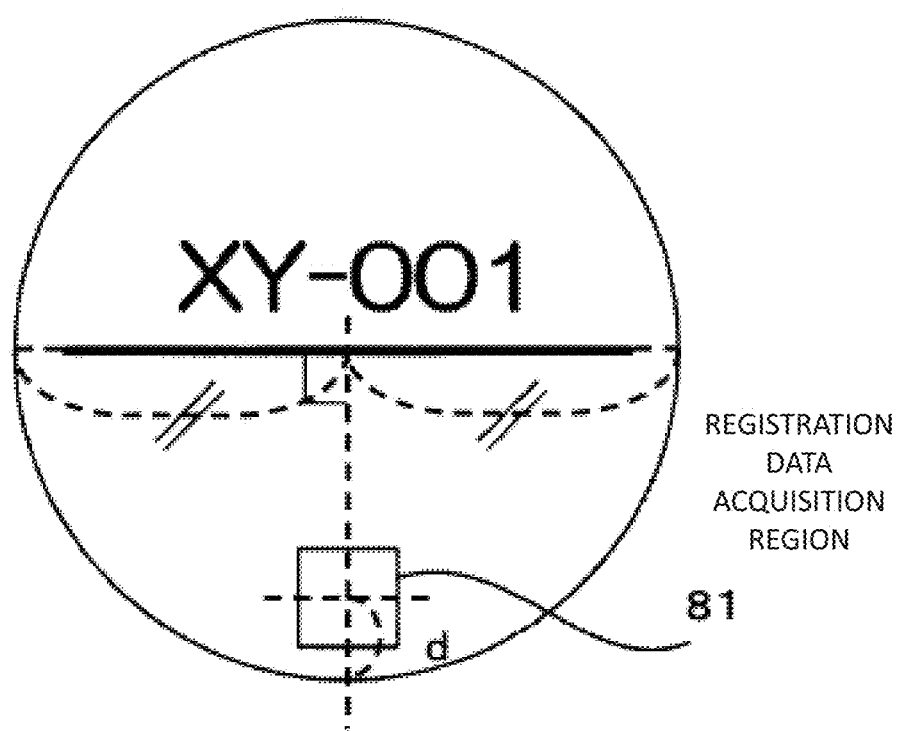
FIG. 33 is a diagram illustrating a procedure when a registration data acquisition unit 22 determines the position of the registration data acquisition region 81.

Specifically, as illustrated in FIG. 33, the registration data acquisition unit 22 determines the position of the registration data acquisition region 81 by the following procedure.

(1) Draw a line segment extending to the circumferential portion (edge portion) of the horizontal line (line) tablet in the printed pattern.

(2) Extend the vertical bisector of the drawn line segment to the side where the characters of "XY-100" are not printed with respect to the horizontal line.

(3) Obtain the position of an intersection point between the vertical bisector and the circumferential portion of the tablet.

(4) Proceed from the intersection point in a central direction of the tablet along the vertical bisector, by a preset distance d.

(5) Determine the registration data acquisition region 81 having the arrival point on the vertical bisector as center coordinates, which proceeds from the intersection point along the vertical bisector by the distance d.

As described above, the degree of the registration data acquisition region 81 changing if printing deviation occurs in a case where the position of the registration data acquisition region 81 is determined based on both the outer shape of the tablet and the printing pattern will be described with reference to FIGS. 34A to 34E.

Figures 34A, 34B, 34C, 34D, 34E:
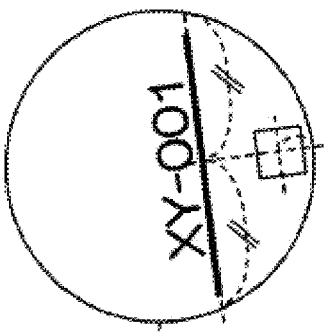
FIGS. 34A to 34E are diagrams illustrating examples of cases where the acquisition region of the registration data is determined based on both the outer shape of a tablet and the printing pattern.

As illustrated in FIG. 34A, in a case where the printing pattern is normally printed, the registration data acquisition region is set at the appropriate position.

As illustrated in FIG. 34C, even in a case where the orientation of the printing pattern slightly inclines, the registration data acquisition region is set at the appropriate position.

As illustrated in FIG. 34B and FIG. 34D, it is understood that the registration data acquisition region is set at the appropriate position even in a case where the printing pattern is printed in a state of being shifted from the center.

As illustrated in FIG. 34E, it is understood that the registration data acquisition region is set at the appropriate position even in a case where the printing pattern is printed in a state of being largely shifted from the center.

Modification Example

In the exemplary embodiments, descriptions are made by using a case where printing is performed only on one side of a tablet. However, the present invention is not limited thereto. The present invention can be also similarly applied to a case where a reversing device that reverses a tablet is provided at the end of the conveyor 60, a set of components of the detection camera 30, the inspection camera 40, the print head section 50, and the like is prepared one more, and thus printing is performed on the reversed tablet.

As described above, FIG. 35 illustrates an example of a printing device that reverses a tablet and performs printing. In the printing device illustrated in FIG. 35, a configuration in which a reversal roller 100 is provided at the end of the conveyor 60 so as to reverse a tablet, and the reversed tablet is conveyed by the conveyor 60*a* is made. A detection camera 30*a*, a print head section 50*a*, and an inspection camera 40*a* which respectively have configurations similar to the detection camera 30, the print head section 50, and the inspection camera 40 provided on the conveyor 60 are provided on a conveyor 60*a* for conveying the reversed tablet. The controller 10 performs processing such as control of the print head section 50*a* based on images of a tablet, which have been picked up by the detection camera 30*a* and the inspection camera 40*a*, and acquisition of registration data, by a method similar to that in the above descriptions.

Figure 35:
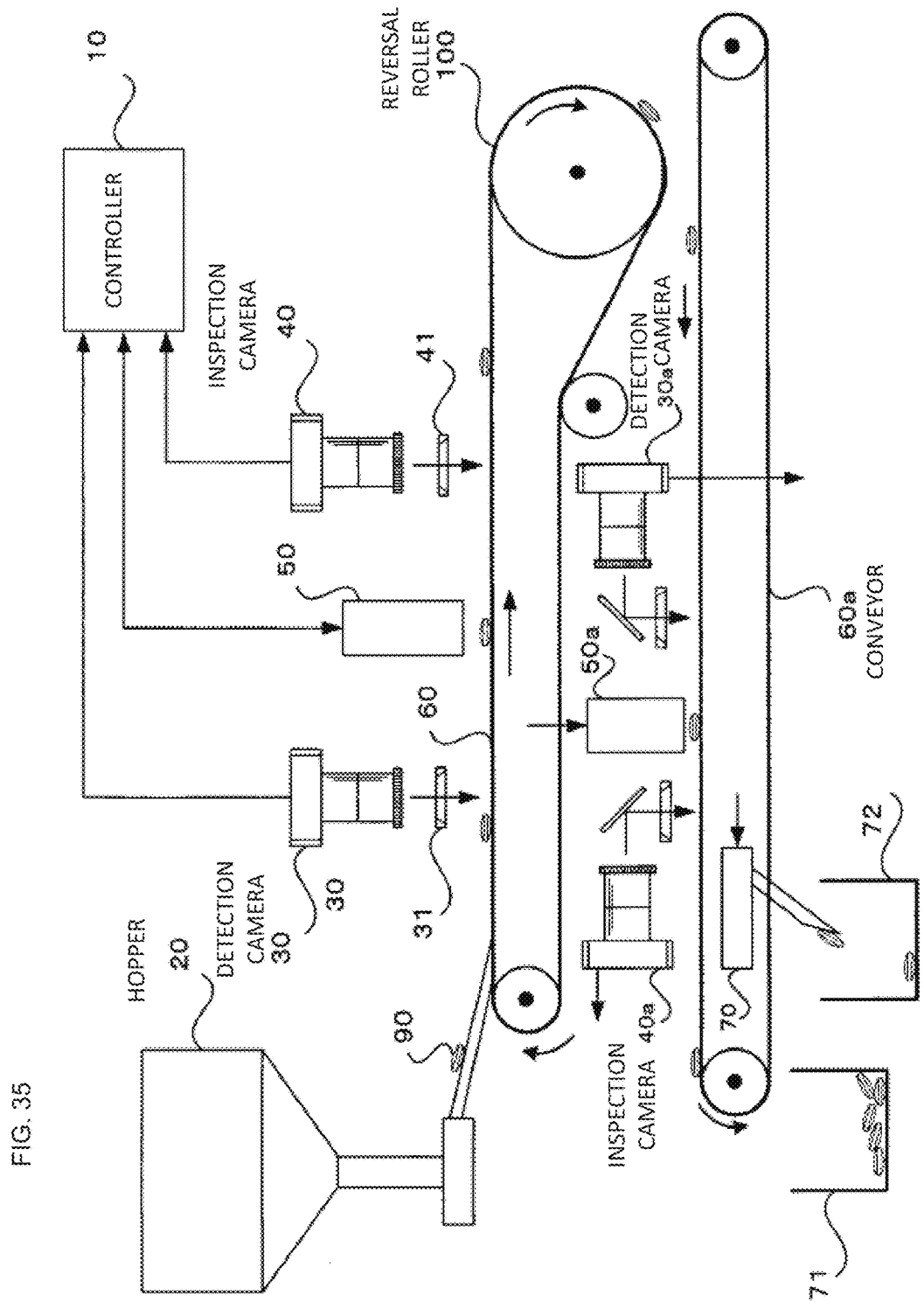
FIG. 35 is a diagram illustrating an example of a printing device that reverses a tablet and performs printing.

It can be realized that characters and the like are printed on both surfaces of a tablet or printing is performed on only a specific surface of a tablet having the front and back surfaces, such as a tablet having a secant line, by using the printing device as illustrated in FIG. 35.

In the printing devices in the exemplary embodiment, for simple descriptions, descriptions are made by using a case where tablets 90 are conveyed on the conveyor 60 in only one row. However, the present invention can be also similarly applied to a case where tablets of rows are conveyed together and printing is performed on tablets together.

In the exemplary embodiments, descriptions are made by using a case where the collation operation is performed in a state where image data of 32×32 dots is acquired as the registration data and image data of 64×64 dots is acquired as the collation data. However, the data size of the registration data and the collation data is not limited to such a size.

Although the present invention is described in detail with reference to the specific exemplary embodiments, it is apparent to those skilled in the art that various changes or modifications can be made without departing from the spirit and the scope of the present invention.

What is claimed is:

1. A printing device comprising:
   a first image pickup unit that picks up a first image including a conveyed object;
   a printing unit that performs printing on the object based on the first image;
   a second image pickup unit that picks up a second image including the object on which printing has been performed by the printing unit;
   a check unit that checks a print state of the object in the second image;
   a first acquisition unit that acquires feature data indicating a feature distributed in a first region of a predetermined size on the object, from one of the first image and the second image, as registration data;
   a second acquisition unit that acquires feature data indicating a feature distributed in a second region of a predetermined size on the object, from the other image of the first image and the second image, as collation data,
   a verification unit that compares the registration data and the collation data and that verifies that reliability of the registration data is equal to or greater than a predetermined criterion value; and
   a storage that stores the registration data as data for determining an identity of the object.

2. The printing device according to claim 1,
   wherein the verification unit computes a correlation value between the registration data and data acquired from the corresponding region in the collation data, and
   the verification unit outputs a verification result that the reliability of the registration data is equal to or greater than the predetermined criterion value in a case where the correlation value satisfies a predetermined criteria.

3. The printing device according to claim 1,
   wherein the second acquisition unit acquires feature data indicating a feature distributed in the second region which includes the first region on the object and has a size larger than that of the first region, as the collation data,
   the verification unit sequentially selects pieces of data having the same size as that of the registration data from the collation data, sequentially computes a correlation value between the selected data and the registration data, and thus acquires a plurality of correlation values, and
   the verification unit outputs a verification result that the reliability of the registration data is equal to or greater than the predetermined criterion value in a case where the maximum value of the plurality of acquired correlation values is equal to or greater than a first predetermined value and a normalized score of the maximum value of the correlation values is equal to or greater than a second predetermined value, the normalized score being obtained by dividing a value obtained by subtracting an average value from the maximum value of the correlation values, by standard deviation.

4. The printing device according to claim 2,
   wherein the verification unit acquires the correlation value by computation with a normalized correlation method.

5. The printing device according to claim 1,
wherein the storage stores an entire image of the object after the printing, as the registration data.

6. The printing device according to claim 1, further comprising a character recognition processing section that performs character recognition processing of information printed on the object after the printing,
wherein the storage stores character information obtained by the character recognition processing section, along with the registration data.

7. The printing device according to claim 1, wherein the storage stores information of a verification result for the registration data in the verification unit, along with the registration data.

8. The printing device according to claim 1, further comprising a suspension section that suspends an operation of the device in a case where a verification result in the verification unit indicates that the reliability of the registration data is smaller than the predetermined criterion value.

9. The printing device according to claim 1, further comprising an output section that outputs the object to an output place in a case where a verification result in the verification unit indicates that the reliability of the registration data is smaller than the predetermined criterion value.

10. The printing device according to claim 1,
wherein the first acquisition unit determines the first region based on a position defined by an outer shape of the object and a position of print information printed on the object.

11. The printing device according to claim 1, further comprising a test data storage section that stores feature data indicating a feature distributed in the first region of a test object having an appearance different from that of a normal object, as test data,
wherein the second acquisition unit acquires feature data indicating a feature distributed in the second region having a predetermined size on the test object, as the collation data, in a case where an object in one of the first image and the second image is the test object, and
the verification unit compares the test data and the collation data and verifies that the device normally operates.

12. The printing device according to claim 11,
wherein the test object is fixed on a conveying path for conveying an object.

13. The printing device according to claim 1, further comprising:
a test data storage section that stores feature data indicating a feature distributed in the first region of a test object, as test data; and
an image pattern of the test data, the image pattern being fixed on a conveying path for conveying an object,
wherein the second acquisition unit acquires the image pattern of the test data, as the collation data, in a case where the image pattern of the test data is included in one of the first image and the second image, and the verification unit compares the test data and the collation data and verifies that the device normally operates.

14. The printing device according to claim 1,
wherein the storage does not store the registration data, but stores at least one part of the first image or the second image acquired for the registration data, as data for determining an identity of the object.

15. The printing device according to claim 1, wherein the object is a tablet.

16. A method for printing, comprising:
picking up a first image including a conveyed object;
performing printing on the object based on the first image;
picking up a second image including the object after the printing is performed;
checking a print state of the object in the second image;
acquiring feature data indicating a feature distributed in a first region of a predetermined size on the object, from one of the first image and the second image, as registration data;
acquiring feature data indicating a feature distributed in a second region of a predetermined size on the object, from the other image of the first image and the second image, as collation data;
comparing the registration data and the collation data and verifying that reliability of the registration data is equal to or greater than a predetermined criterion value; and
storing the registration data as data for determining an identity of the object.

17. A non-transitory computer readable medium storing a program causing a computer to execute a process for printing, the process comprising:
picking up a first image including a conveyed object;
performing printing on the object based on the first image;
picking up a second image including the object after the printing is performed;
checking a print state of the object in the second image;
acquiring feature data indicating a feature distributed in a first region of a predetermined size on the object, from one of the first image and the second image, as registration data;
acquiring feature data indicating a feature distributed in a second region of a predetermined size on the object, from the other image of the first image and the second image, as collation data;
comparing the registration data and the collation data and verifying that reliability of the registration data is equal to or greater than a predetermined criterion value; and
storing the registration data as data for determining an identity of the object.

18. The printing device according to claim 3,
wherein the verification unit acquires the correlation value by computation with a normalized correlation method.

19. The printing device according to claim 2,
wherein the storage stores an entire image of the object after the printing, as the registration data.

20. The printing device according to claim 3,
wherein the storage stores an entire image of the object after the printing, as the registration data.

* * * * *